United States Patent
Turano et al.

(10) Patent No.: US 8,581,040 B2
(45) Date of Patent: Nov. 12, 2013

(54) METHODS OF PRODUCING GABA

(75) Inventors: Frank J. Turano, Baltimore, MD (US); Kathleen A. Turano, Baltimore, MD (US)

(73) Assignee: Plant Sensory Systems, LLC, Baltimore, MD (US)

( * ) Notice: Subject to any disclaimer, the term of this patent is extended or adjusted under 35 U.S.C. 154(b) by 55 days.

(21) Appl. No.: 13/095,243

(22) Filed: Apr. 27, 2011

(65) Prior Publication Data

US 2011/0203019 A1 Aug. 18, 2011

Related U.S. Application Data

(63) Continuation-in-part of application No. 12/201,648, filed on Aug. 29, 2008, now Pat. No. 8,106,261.

(60) Provisional application No. 60/968,964, filed on Aug. 30, 2007, provisional application No. 60/986,640, filed on Nov. 9, 2007.

(51) Int. Cl.
*A01H 5/00* (2006.01)
*C12N 15/82* (2006.01)
*C12N 15/52* (2006.01)
*C12N 9/10* (2006.01)
*C12N 9/04* (2006.01)
*C12N 15/62* (2006.01)
*C12P 21/02* (2006.01)
*A61K 38/00* (2006.01)

(52) U.S. Cl.
USPC ............ 800/281; 800/287; 800/288; 800/298; 800/320.1; 800/302; 800/290; 800/289; 435/468; 435/419; 435/190; 435/193; 435/69.8; 435/70.1; 514/1.1

(58) Field of Classification Search
None
See application file for complete search history.

(56) References Cited

U.S. PATENT DOCUMENTS

| 5,439,873 | A | 8/1995 | Kinnersley |
| 7,314,974 | B2 | 1/2008 | Cao |
| 2003/0046732 | A1 | 3/2003 | Kinnersley et al. |
| 2003/0110530 | A1 | 6/2003 | Shelp et al. |
| 2003/0233675 | A1 | 12/2003 | Cao |
| 2004/0137586 | A1 | 7/2004 | Huisman |
| 2004/0177398 | A1 | 9/2004 | Palaivelu et al. |

FOREIGN PATENT DOCUMENTS

| WO | WO 00/61763 | | 10/2000 |
| WO | WO 02/077183 | A2 | 10/2002 |

OTHER PUBLICATIONS

Samsonova et al (BMC Microbiology Jan. 31, 2003:3(1):2).*
Samsonova et al., BMC Microbiology, Jan. 31, 2003, 3(1):2.
Samsonova et al., FEBS Letters 579, 2005, pp. 4107-4112.
Wink, Plant Biochemistry, Academic Press, 1997.
Shaine et al., Journal of Bacteriology, 1985, (163)3, pp. 933-937.
Huang et al., The Plant Cell, 1990, vol. 2, pp. 1249-1260.
"Novel Genes With Non-Canonical Start Codons Found in *Escherichia coli* K12," 2002, Anton Forsberg, Arne Elofsson, Leif Isaksson, Stockholm Bioinformatics Center, Stockholm University.

* cited by examiner

*Primary Examiner* — David T Fox
*Assistant Examiner* — Lee A Visone
(74) *Attorney, Agent, or Firm* — Rothwell, Figg, Ernst & Manbeck P.C.

(57) ABSTRACT

The present invention describes an alternative approach to increase GABA production in prokaryotes or eukaryotes, namely by the insertion of the putrescine catabolic pathway in organisms where the pathway does not exist or has not clearly been identified. The invention describes methods for the use of polynucleotides that encode functional putrescine aminotransferase (PAT) and gamma-aminobutyricaldehyde dehydrogenase (GABAlde DeHase) polypeptides in plants to increase GABA production. The preferred embodiment of the invention is in plants but other organisms may be used. Changes in GABA availability will improve growth and increase tolerance to biotic and abiotic stress.

39 Claims, 2 Drawing Sheets

SEQUENCE LISTING

```
<160> NUMBER OF SEQ ID NOS: 52

<210> SEQ ID NO 1
<211> LENGTH: 1383
<212> TYPE: DNA
<213> ORGANISM: E. coli
```

<400> SEQUENCE: 1

```
atgttgaaca ggttaccttc gagcgcatcg gctttagcgt gcagcgccca cgccctgaat        60
ctcattgaga agcgaacgct ggatcatgag gagatgaaag cacttaaccg agaggtgatt       120
gaatacttca aagagcatgt caatccgggg tttttagagt atcgcaaatc tgttaccgcc       180
ggcggggatt acggagccgt agagtggcaa gcgggaagtt taaatacgct tgtcgacacc       240
cagggccagg agtttatcga ctgcctggga ggttttggaa ttttcaacgt ggggcaccgt       300
aatccagttg tggtttccgc cgtacagaat caacttgcga acaaccgct gcacagccag        360
gagctgctcg atccgttacg ggcgatgttg gcgaaaaccc ttgctgcgct aacgcccggt       420
aaactgaaat acagcttctt ctgtaatagc ggcaccgagt ccgttgaagc agcgctgaag       480
ctggcgaaag cttaccagtc accgcgcggc aagtttactt ttattgccac cagcggcgcg       540
ttccacggta aatcacttgg cgcgctgtcg gccacggcga aatcgacctt ccgcaaaccg       600
tttatgccgt tactgccggg cttccgtcat gtgccgtttg caatatcga agccatgcgc        660
acggctctta cgagtgcaa aaaaaccggt gatgatgtgg ctgcggtgat cctcgaaccg        720
attcagggtg aaggtggcgt aattctgccg ccgccgggct atctcaccgc cgtacgtaag       780
ctatgcgatg agttcggcgc actgatgatc ctcgatgaag tacaaacggg catggggcgc       840
acgggcaaga tgttcgcctg cgagcatgag aacgtacagc cggatatcct ctgccttgcc       900
aaagcgctcg gcggcggcgt gatgccgatt ggcgcgacca tcgccactga gaggtgtttt      960
tcagttctgt tcgacaaccc attcctgcat accaccacct tggcggcaa cccgctggcc       1020
tgtgcggcgg cgctggcgac catcaatgtg ttgctggagc agaacttacc ggctcaggct      1080
gagcaaaaag cgatatgtt gctggacggt ttccgtcaac tggcgcggga atatcccgat       1140
ctggtacagg aagcgcgtgg taaagggatg ttgatggcga ttgagtttgt tgataacgaa      1200
atcggctata actttgccag cgagatgttc cgccagcgcg tactggtggc cggaacgctc      1260
aataacgcca aaacgatccg cattgaaccg ccactgacac tgaccattga acagtgtgaa     1320
ctggtgatca aagcggcgcg taaggcgctg gcggccatgc gagtaagtgt cgaagaagcg     1380
taa                                                                    1383
```

<210> SEQ ID NO 2
<211> LENGTH: 459
<212> TYPE: PRT
<213> ORGANISM: E. coli

<400> SEQUENCE: 2

```
Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110
```

```
Lys Gln Pro Leu His Ser Gln Glu Leu Leu Asp Pro Leu Arg Ala Met
            115                 120                 125

Leu Ala Lys Thr Leu Ala Ala Leu Thr Pro Gly Lys Leu Lys Tyr Ser
130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
        260                 265                 270

Val Gln Thr Gly Met Gly Arg Thr Gly Lys Met Phe Ala Cys Glu His
    275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 3
<211> LENGTH: 1425
<212> TYPE: DNA
<213> ORGANISM: E. coli

<400> SEQUENCE: 3
atgcaacata agttactgat taacggagaa ctggttagcg gcgaagggga aaaacagcct      60
gtctataatc cggcaacggg ggacgtttta ctggaaattg ccgaggcatc cgcagagcag     120
gtcgatgctg ctgtgcgcgc ggcagatgca gcatttgccg aatgggggca aaccacgccg     180
```

```
aaagtgcgtg cggaatgtct gctgaaactg gctgatgtta tcgaagaaaa tggtcaggtt    240
tttgccgaac tggagtcccg taattgtggc aaaccgctgc atagtgcgtt caatgatgaa    300
atcccggcga ttgtcgatgt ttttcgcttt ttcgcgggtg cggcgcgctg tctgaatggt    360
ctggcggcag gtaatatctg aaggtcat acttcgatga tccgtcgcga tccgttgggg    420
gtcgtggctt ctatcgcacc gtggaattat ccgctgatga tggccgcgtg gaaacttgct    480
ccggcgctgg cggcagggaa ctgcgtagtg cttaaaccat cagaaattac cccgctgacc    540
gcgttgaagt tggcagagct ggcgaaagat atcttcccgg caggcgtgat taacatactg    600
tttggcagag caaaacggt gggtgatccg ctgaccggtc atcccaaagt gcggatggtg    660
tcgctgacgg gctctatcgc accggcgag cacatcatca gccataccgc gtcgtccatt    720
aagcgtactc atatggaact tggtggcaaa gcgccagtga ttgttttttga tgatgcggat    780
attgaagcag tggtcgaagg tgtacgtaca tttggctatt acaatgctgg acaggattgt    840
actgcggctt gtcggatcta cgcgcaaaaa ggcatttacg atacgctggt ggaaaaactg    900
ggtgctgcgg tggcaacgtt aaaatctggt gcgccagatg acgagtctac ggagcttgga    960
cctttaagct cgctggcgca tctcgaacgc gtcggcaagg cagtagaaga ggcgaaagcg   1020
acagggcaca tcaaagtgat cactggcggt gaaaagcgca agggtaatgg ctattactat   1080
gcgccgacgc tgctggctgg cgcattacag gacgatgcca tcgtgcaaaa agaggtattt   1140
ggtccagtag tgagtgttac gcccttcgac aacgaagaac aggtggtgaa ctgggcgaat   1200
gacagccagt acggacttgc atcttcggta tggacgaaag atgtgggcag ggcgcatcgc   1260
gtcagcgcac ggctgcaata tggttgtacc tgggtcaata cccatttcat gctggtaagt   1320
gaaatgccgc acggtgggca gaaactttct ggttacggca aggatatgtc actttatggg   1380
ctggaggatt acaccgtcgt ccgccacgtc atggttaaac attaa              1425
```

<210> SEQ ID NO 4
<211> LENGTH: 474
<212> TYPE: PRT
<213> ORGANISM: E. coli

<400> SEQUENCE: 4

```
Met Gln His Lys Leu Leu Ile Asn Gly Glu Leu Val Ser Gly Glu
1               5                   10                  15

Glu Lys Gln Pro Val Tyr Asn Pro Ala Thr Gly Asp Val Leu Leu Glu
            20                  25                  30

Ile Ala Glu Ala Ser Ala Glu Gln Val Asp Ala Val Arg Ala Ala
        35                  40                  45

Asp Ala Ala Phe Ala Glu Trp Gly Gln Thr Thr Pro Lys Val Arg Ala
    50                  55                  60

Glu Cys Leu Leu Lys Leu Ala Asp Val Ile Glu Asn Gly Gln Val
65                  70                  75                  80

Phe Ala Glu Leu Glu Ser Arg Asn Cys Gly Lys Pro Leu His Ser Ala
                85                  90                  95

Phe Asn Asp Glu Ile Pro Ala Ile Val Asp Val Phe Arg Phe Phe Ala
            100                 105                 110

Gly Ala Ala Arg Cys Leu Asn Gly Leu Ala Ala Gly Glu Tyr Leu Glu
        115                 120                 125

Gly His Thr Ser Met Ile Arg Arg Asp Pro Leu Gly Val Val Ala Ser
    130                 135                 140

Ile Ala Pro Trp Asn Tyr Pro Leu Met Met Ala Ala Trp Lys Leu Ala
145                 150                 155                 160
```

```
Pro Ala Leu Ala Ala Gly Asn Cys Val Val Leu Lys Pro Ser Glu Ile
            165                 170                 175

Thr Pro Leu Thr Ala Leu Lys Leu Ala Glu Leu Ala Lys Asp Ile Phe
        180                 185                 190

Pro Ala Gly Val Ile Asn Ile Leu Phe Gly Arg Gly Lys Thr Val Gly
    195                 200                 205

Asp Pro Leu Thr Gly His Pro Lys Val Arg Met Val Ser Leu Thr Gly
    210                 215                 220

Ser Ile Ala Thr Gly Glu His Ile Ile Ser His Thr Ala Ser Ser Ile
225                 230                 235                 240

Lys Arg Thr His Met Glu Leu Gly Gly Lys Ala Pro Val Ile Val Phe
            245                 250                 255

Asp Asp Ala Asp Ile Glu Ala Val Val Glu Gly Val Arg Thr Phe Gly
        260                 265                 270

Tyr Tyr Asn Ala Gly Gln Asp Cys Thr Ala Ala Cys Arg Ile Tyr Ala
    275                 280                 285

Gln Lys Gly Ile Tyr Asp Thr Leu Val Glu Lys Leu Gly Ala Ala Val
    290                 295                 300

Ala Thr Leu Lys Ser Gly Ala Pro Asp Asp Glu Ser Thr Glu Leu Gly
305                 310                 315                 320

Pro Leu Ser Ser Leu Ala His Leu Glu Arg Val Gly Lys Ala Val Glu
            325                 330                 335

Glu Ala Lys Ala Thr Gly His Ile Lys Val Ile Thr Gly Gly Glu Lys
        340                 345                 350

Arg Lys Gly Asn Gly Tyr Tyr Tyr Ala Pro Thr Leu Leu Ala Gly Ala
    355                 360                 365

Leu Gln Asp Asp Ala Ile Val Gln Lys Glu Val Phe Gly Pro Val Val
    370                 375                 380

Ser Val Thr Pro Phe Asp Asn Glu Glu Gln Val Val Asn Trp Ala Asn
385                 390                 395                 400

Asp Ser Gln Tyr Gly Leu Ala Ser Ser Val Trp Thr Lys Asp Val Gly
            405                 410                 415

Arg Ala His Arg Val Ser Ala Arg Leu Gln Tyr Gly Cys Thr Trp Val
        420                 425                 430

Asn Thr His Phe Met Leu Val Ser Glu Met Pro His Gly Gly Gln Lys
    435                 440                 445

Leu Ser Gly Tyr Gly Lys Asp Met Ser Leu Tyr Gly Leu Glu Asp Tyr
    450                 455                 460

Thr Val Val Arg His Val Met Val Lys His
465                 470

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
ttttggtacc cacatttgca aaatgatgaa tg                                  32

<210> SEQ ID NO 6
<211> LENGTH: 32
<212> TYPE: DNA
<213> ORGANISM: Artificial Sequence
<220> FEATURE:
<223> OTHER INFORMATION: primer
```

```
<400> SEQUENCE: 6
ttttggatcc ccaatctggt taccgcattg ac                              32

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
ttttggatcc atgttgaaca ggttaccttc ga                              32

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
tttttctaga ttacgcttct tcgacactta ct                              32

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
tttttctaga taccgagctc gaatttcccc ga                              32

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
ttttctgcag gatctagtaa catagatgac ac                              32

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ttttgagctc atgcaacata agttactgat ta                              32

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
tttttctaga ttaatgttta accatgacgt gg                              32

<210> SEQ ID NO 13
<211> LENGTH: 32
<212> TYPE: DNA
```

```
<213> ORGANISM: Artificial Sequence
<220> FEATURE:
<223> OTHER INFORMATION: primer

<400> SEQUENCE: 13
ttttggtacc tcttaccttg tcctgcaacg ag                                32

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
ttttgagctc ctttgtttct gtttagtgaa ag                                32

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
ttttgagctc atgttgaaca ggttaccttc ga                                32

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
tttttctaga ttacgcttct tcgacactta ct                                32

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
ttttgagctc atgcaacata agttactgat ta                                32

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
tttttctaga ttaatgttta accatgacgt gg                                32

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19
ttttggtacc accaaaggat accctgattt g                                 31
```

<210> SEQ ID NO 20
<211> LENGTH: 42
<212> TYPE: DNA
<213> ORGANISM: Artificial Sequence
<220> FEATURE:
<223> OTHER INFORMATION: primer

<400> SEQUENCE: 20
cgctcgaagg taacctgttc atcacggaga tgagagagag ag        42

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
atgaacaggt taccttcgag cg        22

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
ttacgcttct tcgacactta ct        22

<210> SEQ ID NO 23
<211> LENGTH: 42
<212> TYPE: DNA
<213> ORGANISM: Artificial Sequence
<220> FEATURE:
<223> OTHER INFORMATION: primer

<400> SEQUENCE: 23
agtaagtgtc gaagaagcgt aagctaccga gctcgaattt cc        42

<210> SEQ ID NO 24
<211> LENGTH: 31
<212> TYPE: DNA
<213> ORGANISM: Artificial Sequence
<220> FEATURE:
<223> OTHER INFORMATION: primer

<400> SEQUENCE: 24
tttttctaga aacgacggcc agtgaattcc c        31

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
tttttttggt accgatattt gagcaaaact gtgg        34

<210> SEQ ID NO 26
<211> LENGTH: 35
<212> TYPE: DNA
<213> ORGANISM: Artificial Sequence
<220> FEATURE:
<223> OTHER INFORMATION: primer

<400> SEQUENCE: 26 tttttttct agagatctag taacatagat gacac         35

<210> SEQ ID NO 27
<211> LENGTH: 44
<212> TYPE: DNA
<213> ORGANISM: Artificial Sequence
<220> FEATURE:
<223> OTHER INFORMATION: primer

<400> SEQUENCE: 27
gttaatcagt aacttatgtt gcatcacgga gatgagagag agag         44

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
atgcaacata agttactgat taac         24

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
ttaatgttta accatgacgt gg         22

<210> SEQ ID NO 30
<211> LENGTH: 42
<212> TYPE: DNA
<213> ORGANISM: Artificial Sequence
<220> FEATURE:
<223> OTHER INFORMATION: primer

<400> SEQUENCE: 30
ccacgtcatg gttaaacatt aagctaccga gctcgaattt cc         42

<210> SEQ ID NO 31
<211> LENGTH: 31
<212> TYPE: DNA
<213> ORGANISM: Artificial Sequence
<220> FEATURE:
<223> OTHER INFORMATION: primer

<400> SEQUENCE: 31
tttttctaga aacgacggcc agtgaattcc c         31

<210> SEQ ID NO 32
<211> LENGTH: 34
<212> TYPE: DNA
<213> ORGANISM: Artificial Sequence
<220> FEATURE:
<223> OTHER INFORMATION: primer

<400> SEQUENCE: 32 tttttttct agagatattt gagcaaaact gtgg         34

<210> SEQ ID NO 33
<211> LENGTH: 35
<212> TYPE: DNA

-continued

<213> ORGANISM: Artificial Sequence
<220> FEATURE:
<223> OTHER INFORMATION: primer

<400> SEQUENCE: 33 ttttttctg caggatctag taacatagat gacac                                35

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
ttttggtacc tcttaccttg tcctgcaacg                                     30

<210> SEQ ID NO 35
<211> LENGTH: 44
<212> TYPE: DNA
<213> ORGANISM: Artificial Sequence
<220> FEATURE:
<223> OTHER INFORMATION: primer

<400> SEQUENCE: 35
cgctcgaagg taacctgttc atctttgttt ctgtttagtg aaag                     44

<210> SEQ ID NO 36
<211> LENGTH: 32
<212> TYPE: DNA
<213> ORGANISM: Artificial Sequence
<220> FEATURE:
<223> OTHER INFORMATION: primer

<400> SEQUENCE: 36
tttttttggt acccgagctt caacgtagcc ac                                  32

<210> SEQ ID NO 37
<211> LENGTH: 44
<212> TYPE: DNA
<213> ORGANISM: Artificial Sequence
<220> FEATURE:
<223> OTHER INFORMATION: primer

<400> SEQUENCE: 37
cgctcgaagg taacctgttc atctttgttt ctgtttagtg aaag                     44

<210> SEQ ID NO 38
<211> LENGTH: 32
<212> TYPE: DNA
<213> ORGANISM: Artificial Sequence
<220> FEATURE:
<223> OTHER INFORMATION: primer

<400> SEQUENCE: 38
tttttttcca tggcgagctt caacgtagcc ac                                  32

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
ccaatgccta ataatgtcta gc                                             22

<210> SEQ ID NO 40
<211> LENGTH: 44
<212> TYPE: DNA
<213> ORGANISM: Artificial Sequence
<220> FEATURE:
<223> OTHER INFORMATION: primer

<400> SEQUENCE: 40
cgctcgaagg taacctgttc atgccgtttg attttgaatt tgag             44

<210> SEQ ID NO 41
<211> LENGTH: 35
<212> TYPE: DNA
<213> ORGANISM: Artificial Sequence
<220> FEATURE:
<223> OTHER INFORMATION: primer

<400> SEQUENCE: 41
tttttttggt accattcttg aattacgatt gtacc                       35

<210> SEQ ID NO 42
<211> LENGTH: 46
<212> TYPE: DNA
<213> ORGANISM: Artificial Sequence
<220> FEATURE:
<223> OTHER INFORMATION: primer

<400> SEQUENCE: 42
gttaatcagt aacttatgtt gcatgccgtt tgattttgaa tttgag           46

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43 tttttttttct agaattcttg aattacgatt gtacc                      35

<210> SEQ ID NO 44
<211> LENGTH: 1380
<212> TYPE: DNA
<213> ORGANISM: Artificial Sequence
<220> FEATURE:
<223> OTHER INFORMATION: Synthetic Construct

<400> SEQUENCE: 44
atggaaaaag aacctatcac caaggacgct agcaaagagt ctgttatcga cgatcttgat      60
gagatcctcg gtttcatcaa gggaaacgag atgaccgatg accaaaagga taagatgacc     120
aaggacaccc tcaactactt cgataactac gtttcacctg atggctcaag tacagaaag     180 tctgtttcta ccgatgctgc tgttcttgag tggactgatc aagatgctgt tatccatgga     240
ctcaagggtg aagagttcat cgattgtctt ggaggattcg aatctacac ttctggacac      300 cgtaacaagt acatcctcga tgctgttaag gctcaacttg agcatcaagc tctccattct     360
caagagcttc tcgatcctct tagaggatac cttgctaagg ctgttgctga tatcactcct     420
ggtgatcttg agaagtgctt cttcactaac ggtggtgctg aggctgttga gatggctctt     480
aaacttgcta gaatcgctac tggtggaagg tggtacatct ctactatcgg agcttttccac    540 ggaaagtcta tggagctat ctctatggga ggaaagggaa cttaccgtaa gccttacatc     600
cctatggttc aacaggttga gcatgttgag tacggaaacg ctgaggatat gagaaaggct     660

-continued

| | |
|---|---|
| atcagaaacc tcgttgctgt tggagagact gttgctgctg ttatcatcga gcctgttcaa | 720 |
| ggtgaggctg aattatcgt tcctcctaag ggatacctca aagaggttag agagatctgc | 780 |
| gacgagtacg gtgttgctct tatcttcgat gagattcagt gcggaatggg aagaactgga | 840 |
| tctatgtggc gttgtgaggc tgaggatgtt gttcctgata tccttactta cggaaaggct | 900 |
| ttcggaggtg aatcatgcc tatcactgga cttatctgta ggcctaagat gtgggttcag | 960 |
| cagcttatcg ataacccttg gcttcttgga tctcctactt tcggaggtaa ccctgtttgt | 1020 |
| tgtgctgctg ctatcgctac tatctcttac atgctcaagg ctgatatccc tggacaagct | 1080 |
| agagctaagg gaaactacct tatccctaag ctccaagctc ttgctgatga gttccctgag | 1140 |
| gttatccaag aagttagagg aatcggactc atgatcggag ttgagttcta ctctgatgag | 1200 |
| atcggatact ctgttgctaa gggactttc gatagaggtg ttcttactgc tggaaccctc | 1260 |
| gttaactcta agactatcag attcgagcct cctgctatca tcgagtacga tcaacttgat | 1320 |
| caggtgatcg agagaatgca tggtgctctt gaggatacca agagaagtt cggactctga | 1380 |

<210> SEQ ID NO 45
<211> LENGTH: 1380
<212> TYPE: DNA
<213> ORGANISM: Artificial Sequence
<220> FEATURE:
<223> OTHER INFORMATION: Synthetic Construct

<400> SEQUENCE: 45

| | |
|---|---|
| atggagaagg agccgatcac caaggacgcc agcaaggaaa gcgtcatcga cgacctggat | 60 |
| gagatcctgg gcttcatcaa gggcaacgag atgaccgacg accaaaagga caagatgacc | 120 |
| aaggacaccc tgaactactt cgacaactac gtgagcccgg gctggctgaa gtacagaaag | 180 |
| tctgtgagca ccgacgccgc tgtgcttgag tggactgatc aggacgctgt gatccatggc | 240 |
| ctgaagggcg aagagttcat cgactgcctg gcggcttcg gcatctacac atctggccac | 300 |
| cgcaacaagt acatcctgga cgctgtgaag gcccagctcg agcatcaggc tctgcactct | 360 |
| caagagttgc tggacccact gagggctac cttgctaagg ctgtggctga tatcacccca | 420 |
| ggcgacctcg agaagtgctt cttcactaat ggcggcgctg aggccgttga gatggctctt | 480 |
| aagctggcca ggatcgctac tggcggcaga tggtacatca gcaccatcgg cgctttccac | 540 |
| ggcaagtcta tgggcgctat cagcatgggc ggcaagggca cttaccgcaa gccgtacatc | 600 |
| ccgatggtgc agcaggtcga gcacgttgag tacggcaacg ctgaggacat gaggaaggcc | 660 |
| attaggaacc tggtggccgt gggcgagact gttgctgctg ttatcatcga gccggtgcag | 720 |
| ggcgaggctg gcatcatcgt gccaccaaag ggctacctga aggaagttcg cgagatctgc | 780 |
| gacgagtacg gcgtggccct gatcttcgat gagatccagt gcggcatggg caggactggc | 840 |
| agcatgtggc gctgcgaggc tgaggatgtg gtgccagata tcctgaccta cggcaaggcc | 900 |
| ttcggcggtg gcatcatgcc aatcactggc ctgatttgcc gcccgaagat gtgggtgcag | 960 |
| cagctgatcg acaacccatg gctgctgggc tctccaactt cggcggcaa tccagtttgc | 1020 |
| tgcgccgctg ctatcgccac catcagctac atgctgaagg ccgatatccc aggccaggct | 1080 |
| agggctaagg gcaactacct gatcccaaag ctccaggctc tggccgatga gttcccagag | 1140 |
| gtgatccaag aggtgagggg catcggcctg atgatcggcg ttgagttcta cagcgacgag | 1200 |
| atcggctact ctgtggccaa gggccttttc gatagggcg ttctgaccgc tggcaccctg | 1260 |
| gtgaacagca agaccatcag gttcgagccg ccagccatca tcgagtacga ccagctggac | 1320 |
| caggtgatcg agaggatgca tggcgctctc gaggacacca aggagaagtt cggcctctga | 1380 |

<210> SEQ ID NO 46
<211> LENGTH: 1431
<212> TYPE: DNA
<213> ORGANISM: Artificial Sequence
<220> FEATURE:
<223> OTHER INFORMATION: Synthetic Construct

<400> SEQUENCE: 46

| | | | | | |
|---|---|---|---|---|---|
| atgttcgtgt | tcaaagagag | aatcctctct | aggtctaacg | ctcatcttaa | ccctcttgag | 60 |
| tgtactcaac | aagctctcca | ttggattcac | tctgatacct | tgtctccaga | tgatatggct | 120 |
| gctctcaatc | aagaggtgct | ctcttgtttc | agggaatatg | ttaaccctgg | attcctcgag | 180 |
| tacagaaagt | ctgttactac | cggtggtgat | tatggtgctg | ttgagtggag | agcatctgga | 240 |
| cctaacactc | ttattgatac | tcagggaaac | gagtaccttg | attgtcttgg | aggatacgga | 300 |
| atcttcaacg | tgggacatag | aaaccctaac | gttatcgctg | ctgttgagtc | tcaacttgct | 360 |
| agacaacctc | tccattctca | agagttgctt | gatcctctta | gaggacttct | tgctaagact | 420 |
| cttgctgctc | ttactcctgg | aaacctcaag | tactcttcct | tctctaactc | tggaaccgag | 480 |
| tctgttgagg | ctgctcttaa | acttgctaag | gcttaccaat | ctcctagggg | aaagtacact | 540 |
| ttcattgctg | ctactggtgc | tttccacgga | aagtctcttg | gtgctctttc | tgctactgct | 600 |
| aagcctgctt | ttagaaggcc | tttcatgcct | cttttgcctg | gatttcatca | tgtggctttc | 660 |
| ggagatatct | ctgctatgag | aaagcaggtt | cagcagtgtc | aaaagactgg | tgatgatgtt | 720 |
| gctgctatca | tccttgagcc | tattcaaggt | gaaggtggtg | ttatcgttcc | tcctgaaaat | 780 |
| taccttcctg | ctgttagggc | tctctgtgat | gaagttggag | ctttgcttat | cctcgatgag | 840 |
| gttcaaactg | gaatgggaag | aaccggaaag | atgtttgctt | gtgagcatta | cggtgtgcag | 900 |
| cctgatattc | tttgtttggc | taaggctctt | ggaggtggtg | tgatgcctat | ggagctact | 960 |
| gttgctactg | aggctgtttt | ctctgttctt | ttcgagaacc | ctttcctcca | cactactact | 1020 |
| tttggaggta | accctcttgc | ttgtgctgct | gctcttgcta | ctgttaatga | gcttctcact | 1080 |
| aagaaccttc | cagagcaagc | tgctattcag | ggagaatttt | tgcttcaagg | acttcaacag | 1140 |
| ctcgctgctg | aataccctca | acttattatt | gaggctaggg | gaatgggact | tcttcaagct | 1200 |
| attgagttca | gaaagaacga | gatcggatac | gctttcgcta | agagctttt | ccagagaaac | 1260 |
| atcctcgttg | ctggaactct | caacaactct | aagtctgtta | gaatcgagcc | tccactcact | 1320 |
| atcactagag | aacaatgcgc | tagagtgctc | aaagaggcta | aggacgttct | caagaaactc | 1380 |
| aacggaacca | tgcctgatga | gaacaagatg | aaggaatacg | ctgttgagtg | a | 1431 |

<210> SEQ ID NO 47
<211> LENGTH: 1242
<212> TYPE: DNA
<213> ORGANISM: Artificial Sequence
<220> FEATURE:
<223> OTHER INFORMATION: Synthetic Construct

<400> SEQUENCE: 47

| | | | | | |
|---|---|---|---|---|---|
| atgaatcctg | atgaaatttt | gcaaaagtat | catgatcata | ttaatcctgg | attggctgat | 60 |
| ttgttgcaat | tgggaggatt | ggctgctgtt | gatgataagg | ctgaaggagc | ttatgtttgg | 120 |
| gatgctgatg | aaataagta | tttggatgct | gttggaggat | atggagtttt | tggattggga | 180 |
| catagacctc | ctaaggttat | tgaaaaggtt | aaggaaactt | tggataagat | gcctttggct | 240 |
| tctaagattt | ttattaattc | ttgtgaagct | gaattgggag | aaaagttgtc | tgaagctact | 300 |
| ggatatcaat | attttatgtt | tttgaattct | ggatctgaag | ctgttgaaac | tgctttgaag | 360 |

```
ttggctagat tgactactgg aaagactaat tttattggaa tgactaatgc ttatcatgga      420
gttacttttg gagctttgtc tgtttctgga agagatgttt ataaggaacc ttttaagcct      480
ttgttgcctg gagttaagat tgttccttttt ggagatgctg aagctttggc taatgctttg      540
gatgatactg ttgctgctgt tattgttgaa cctattcaag agaaggagg agttaatgtt       600 cctcctcctg atatttgaa gaaggttaga caattgtgtg atgaagctgg atgttttttg       660
attttggatg aaattcaaac tggaatggga agaactggaa agttgttggc tgaagaatgg      720
gaagatgtta aggctgatat tgtttgtttg ggaaaggctt gggaggagg agttgttcct       780 attggagctg ttggagctac tgaaactgct tggcaaggat ttattgataa tccttttgatt     840 catgaatcta cttttggagg aaatcctttg gctacttctg ctggaattgc tgctgttgat      900
gaaattgttg aaagcaaat ttggaataat gctcattcta ctggagataa gttgttgtct       960
gctttgagat ctgaagctga aaagtatcct catttgatta aggaagttag aggaagagga     1020
ttgttgattg gagttgaaat gatggaagaa ggatatggat tgcctatgat gggatttatg     1080
ttggaagaaa agactttggt tgcttatact ttgaataatc ctagagttat tagaattgaa     1140
cctcctttga ttattggaga tgaagaaatt caatggttgg ttaatgcttt tcaaaaggct     1200
ttggctaagt tggataagtt ggctaaggat ttggaagttt ga                        1242

<210> SEQ ID NO 48
<211> LENGTH: 1236
<212> TYPE: DNA
<213> ORGANISM: Artificial Sequence
<220> FEATURE:
<223> OTHER INFORMATION: Synthetic Construct

<400> SEQUENCE: 48
atgactttgt ttgaacaatt tgaaagacat attaatcctg gattggctgg attgttgaga      60
tttactggat tggataaggt tgaatctcat gctgaaggag tttatgtttg ggatactgaa     120
ggaaagagat atttggattt tttgggattg tatggaactt tgtctttggg acatagacat     180
cctaaggttg ttgctgctgt taaggctcaa ttggataaga tgcctatgtc tgttagagtt     240
atggtttctg aacctactac taagttggct gctagattgg ctgaaattac tcctggagaa     300
ttgtctatgg tttattttgg aaattctgga actgaaggag ttgaagctgc tttgaagttt     360
gctagatttt atactggaaa gcctggattt attactactc aaggaggata tcatggaaag     420
actttgggag ctttgtctgt tactcctaga gaacattatc aattgcctgc tagacctttg     480
gttcctggag ttactgttgt tccttatgga gatgctcaag ctattgaagc tgctattgga     540
cctgatactg ctgctgttat tgttgaacct attcaggaag aaggaggaat tagagttcct     600
cctgaaggat atttgagaga agttagaaga attactagaa aaagggagt tttgatgatt      660 gctgatgaag ttcaaactgg attgggaaga actggaagat tgtggctgt tgattgggaa      720 gaagttgaac tgatatttt ggtttctgct aaggctttgg gaggaggagt tatgcctatt      780
tctgctacta tttgtagacc tgaaattttg tctatttata agactgaacc tttgattcat     840
tctactactt ttgaggaaaa tcctttggct gctgctgctg ctttggctgc tattgaagtt     900
actttggaag aagatatgcc tgctagagct ttggaaatgg acaatatttt gatggctcaa     960
ttgggatctt tgcaacaagc ttatcctgaa tttattcaag aagttagagg aagaggattg    1020
ttggttggat tggaatttac tgatgctgat attggagctg ttgttgttgc tgaattggct    1080
gctagaggag ttttgactgc ttttggattg aataatccta aggttgttag attggaacct    1140
cctttgattg ttgaaaaggc tcatattgat gaatgtttgg aagctttgga aggagctttg    1200
```

<210> SEQ ID NO 49
<211> LENGTH: 1503
<212> TYPE: DNA
<213> ORGANISM: Artificial Sequence
<220> FEATURE:
<223> OTHER INFORMATION: Synthetic Construct

<400> SEQUENCE: 49

```
atgcaaaatt ttgctactaa gactgaattt aagggaaatt atattgatgg aagatggcaa      60
cctgctcatt tggagatag aagacaagtt tataatcctg ctactggaga tttgattgga     120
gaagttgctg aatcttctgt ttctgatgct agagaagcta ttgctgctgc taagaagtct     180
tttatcaaa ctagagaatg gagagattct gatactcaag ctagagctga tatgatttat     240
aagattgctg aaaaggttaa tgaaaataga gaagaattgg cttatttgga tactattgat     300
aatggaaagc ctttgagaga agctcaagga gatgttgatg atgcttatca ttgttttttg     360
tattatgctg gattgattaa ggctccttct ggaggatctt atggagttaa tgatggattt     420
ggaaagatgc attcttatat ggttcatgaa cctgttggag tttgtgctca aattgttcct     480
tggaattatc ctttgttgat gggagtttgg aagttggctc ctgctttggc tgctggaaat     540
tctgttgttt ttaagccttc tgaaattact cctttgtcta ctgttagatt gtttgatatt     600
tttgatgaag ttggattgcc tgctggaact gctaatttgg ttattggaac tggagaaaga     660
gttggagctg aattggctag atctcaagat gttgatatga ttacttttac tggatctact     720
actgttggaa gatctattat gagatctgct gctgataatg ttaagaagat tggattggaa     780
ttgggaggaa agtctcctaa tattattttt tctgatgctg attttgaagg agctattgaa     840
tgggctatgt tgggaatttt tttgaatcaa ggagaaattt gttctgctgg atctagaatt     900
attattgaag aatctttgaa gaataagttt gttttgaagt tgaaggaaag agctgaagct     960
ttgactattg gaaatggatt ggataatcct gatatgggac ctttggtttc tagacatcaa    1020
atgagaagag ttttggaata tattcaaatt ggaaaggatg aaggagctaa gttggttttgt    1080
ggaggatatc aattgactaa tactccttat gatttgggaa attttattgc tcctactatt    1140
tttgatgatt gtacttcttc tatgaagatt gttaaggaag aaattttttgg acctgttgtt    1200
actattcaaa ctttttagaaa tgaacaagaa gctattaagt tggctaatga tactcaatat    1260
ggattggctg agctgttttt tactaaggat ggagctaagg ctttgagagt tattaaggaa    1320
attagagctg gaattacttg gattaattgt tataatccta cttttaatga agctccttgg    1380
ggaggatata agatgtctgg aattggaaga gaattgggag aagatggatt gttggaatat    1440
caagaaacta agcaaattaa tattaatttg aatcctggac ctgttggatg gtatattcat    1500
tag                                                                 1503
```

<210> SEQ ID NO 50
<211> LENGTH: 1425
<212> TYPE: DNA
<213> ORGANISM: Artificial Sequence
<220> FEATURE:
<223> OTHER INFORMATION: Synthetic Construct

<400> SEQUENCE: 50

```
atgcatgata agttgctcat cgagggaaag ttgattgctg aaatggtgaa agctctcgct      60
gttttaatc ctgctactgg tgagcaaatc gctgctattc ctcaagctga tctccatcaa     120
atcgatgctg ctgttcttgc tgctgaatct gcttttgctc attgggggaca aactactcct     180
```

```
aagactagag ctactttgct cctcaagatc gctgatgcta ttgaagagaa cgctgaggtt    240
ttcgctaagt tggagtctct taactgcgga aagccttacc atgctgttct caatgatgag    300
gttccagctg ttgctgatgt gtttagattt tttgctggtg ctgctagatg cctttctgga    360
tctgctgctg gtgaatatct tgagggacac acttctatga tcagaagaga tcctgttgga    420
gttgtggctt ctattgctcc ttggaattac cctctcatga tggctagttg gaaacttgct    480
cctgctttgg ctgctggaaa ctgtgttgtt cttaagcctg ctgagcagac tcctcttact    540 acttttacc ttgctcacct cctcgctgat attcttcctg ctggtgttgt taacatcgtg    600
tttggaagag gtgctgatat cggagatgct cttactggac atgagaaggt taacatggtg    660
tctctcactg gatctattgc tactggtgct catatccttg ctcatactgc tgcttcagtg    720
aagagaactc atatggaact tggaggaaag gctcctgtta tcgttttcga tgatgctgat    780
atcgatcagg tggtggatgg aattagatct ttcggattct acaacgctgg acaagattgc    840
actgctgctt gtagacttta cgttcaaagg gctgtgtacg atgaagttgt tgaagctctt    900
ggaaaggctg ttgctactct taagatcgga gatcctagag atgagactac tgaacttgga    960
cctcttatca ctgagcctca acttgaaaga gtgatgggaa ttgttgagag agctaaggct   1020
ctccctcata ttactgttgt tactggtggt gagagagtga agggaactgg attttacttc   1080
cagcctacag ttcttgctgg tgctaagcaa gatgatgaga tcgttcagaa agaggtgttc   1140
ggacctgtta tctctatcac ctctttcgat gatgaggctc aagttattgg atgggctaac   1200
gcttctaact acggacttgc ttcttctgtg tggactagag atattggaag ggctcataga   1260
cttgctgctt gccttcaata tggatgcact tgggtgaaca ctcatttcat gctcgtttct   1320
gagatgcctc atggtggaca aaagttgtct ggatacggaa aggatatgtc tatgtacgga   1380
ctcgaggatt acactatcgt gagacacatc atgatcaggc actga                   1425
```

<210> SEQ ID NO 51
<211> LENGTH: 459
<212> TYPE: PRT
<213> ORGANISM: Artificial Sequence
<220> FEATURE:
<223> OTHER INFORMATION: synthetic construct

<400> SEQUENCE: 51

```
Met Glu Lys Glu Pro Ile Thr Lys Asp Ala Ser Lys Glu Ser Val Ile
 1               5                  10                  15

Asp Asp Leu Asp Glu Ile Leu Gly Phe Ile Lys Gly Gln Glu Met Thr
             20                  25                  30

Asp Asp Asn Lys Asp Lys Met Thr Lys Asp Thr Leu Gln Tyr Phe Asp
         35                  40                  45

Gln Tyr Val Ser Pro Gly Trp Leu Lys Tyr Arg Lys Ser Val Ser Thr
     50                  55                  60

Asp Ala Ala Val Leu Glu Trp Thr Asp Asn Asp Ala Val Ile His Gly
 65                  70                  75                  80

Leu Lys Gly Glu Glu Phe Ile Asp Cys Leu Gly Gly Phe Gly Ile Tyr
                 85                  90                  95

Thr Ser Gly His Arg Gln Lys Tyr Ile Leu Asp Ala Val Lys Ala Asn
            100                 105                 110

Leu Glu His Asn Ala Leu His Ser Asn Glu Leu Leu Asp Pro Leu Arg
        115                 120                 125

Gly Tyr Leu Ala Lys Ala Val Ala Asp Ile Thr Pro Gly Asp Leu Glu
    130                 135                 140

Lys Cys Phe Phe Thr Gln Gly Gly Ala Glu Ala Val Glu Met Ala Leu
```

```
                145                 150                 155                 160
Lys Leu Ala Arg Ile Ala Thr Gly Gly Arg Trp Tyr Ile Ser Thr Ile
                165                 170                 175

Gly Ala Phe His Gly Lys Ser Met Gly Ala Ile Ser Met Gly Gly Lys
            180                 185                 190

Gly Thr Tyr Arg Lys Pro Tyr Ile Pro Met Val Asn Val Glu His
        195                 200                 205

Val Glu Tyr Gly Gln Ala Glu Asp Met Arg Lys Ala Ile Arg Gln Leu
    210                 215                 220

Val Ala Val Gly Glu Thr Val Ala Ala Val Ile Ile Glu Pro Val Asn
225                 230                 235                 240

Gly Glu Ala Gly Ile Ile Val Pro Pro Lys Gly Tyr Leu Lys Glu Val
                245                 250                 255

Arg Glu Ile Cys Asp Glu Tyr Gly Val Ala Leu Ile Phe Asp Glu Ile
                260                 265                 270

Asn Cys Gly Met Gly Arg Thr Gly Ser Met Trp Arg Cys Glu Ala Glu
            275                 280                 285

Asp Val Val Pro Asp Ile Leu Thr Tyr Gly Lys Ala Phe Gly Gly Gly
    290                 295                 300

Ile Met Pro Ile Thr Gly Leu Ile Cys Arg Pro Lys Met Trp Val Asn
305                 310                 315                 320

Asn Leu Ile Asp Gln Pro Trp Leu Leu Gly Ser Pro Thr Phe Gly Gly
                325                 330                 335

Gln Pro Val Cys Cys Ala Ala Ile Ala Thr Ile Ser Tyr Met Leu
            340                 345                 350

Lys Ala Asp Ile Pro Gly Asn Ala Arg Ala Lys Gly Gln Tyr Leu Ile
        355                 360                 365

Pro Lys Leu Asn Ala Leu Ala Asp Glu Phe Pro Glu Val Ile Asn Glu
    370                 375                 380

Val Arg Gly Ile Gly Leu Met Ile Gly Val Glu Phe Tyr Ser Asp Glu
385                 390                 395                 400

Ile Gly Tyr Ser Val Ala Lys Gly Leu Phe Asp Arg Gly Val Leu Thr
                405                 410                 415

Ala Gly Thr Leu Val Gln Ser Lys Thr Ile Arg Phe Glu Pro Pro Ala
            420                 425                 430

Ile Ile Glu Tyr Asp Asn Leu Asp Asn Val Ile Glu Arg Met His Gly
        435                 440                 445

Ala Leu Glu Asp Thr Lys Glu Lys Phe Gly Leu
    450                 455

<210> SEQ ID NO 52
<211> LENGTH: 474
<212> TYPE: PRT
<213> ORGANISM: Artificial Sequence
<220> FEATURE:
<223> OTHER INFORMATION: synthetic construct

<400> SEQUENCE: 52

Met His Asp Lys Leu Leu Ile Glu Gly Lys Leu Ile Ala Gly Gln Gly
1               5                   10                  15

Glu Ala Leu Ala Val Phe Gln Pro Ala Thr Gly Glu Asn Ile Ala Ala
            20                  25                  30

Ile Pro Asn Ala Asp Leu His Asn Ile Asp Ala Ala Val Leu Ala Ala
        35                  40                  45

Glu Ser Ala Phe Ala His Trp Gly Asn Thr Thr Pro Lys Thr Arg Ala
    50                  55                  60
```

```
Thr Leu Leu Leu Lys Ile Ala Asp Ala Ile Glu Glu Gln Ala Glu Val
 65                  70                  75                  80

Phe Ala Lys Leu Glu Ser Leu Gln Cys Gly Lys Pro Tyr His Ala Val
                 85                  90                  95

Leu Gln Asp Glu Val Pro Ala Val Ala Asp Val Phe Arg Phe Phe Ala
            100                 105                 110

Gly Ala Ala Arg Cys Leu Ser Gly Ser Ala Ala Gly Glu Tyr Leu Glu
        115                 120                 125

Gly His Thr Ser Met Ile Arg Arg Asp Pro Val Gly Val Val Ala Ser
    130                 135                 140

Ile Ala Pro Trp Gln Tyr Pro Leu Met Met Ala Ser Trp Lys Leu Ala
145                 150                 155                 160

Pro Ala Leu Ala Ala Gly Gln Cys Val Val Leu Lys Pro Ala Glu Asn
                165                 170                 175

Thr Pro Leu Thr Thr Phe Tyr Leu Ala His Leu Leu Ala Asp Ile Leu
            180                 185                 190

Pro Ala Gly Val Val Gln Ile Val Phe Gly Arg Gly Ala Asp Ile Gly
        195                 200                 205

Asp Ala Leu Thr Gly His Glu Lys Val Gln Met Val Ser Leu Thr Gly
    210                 215                 220

Ser Ile Ala Thr Gly Ala His Ile Leu Ala His Thr Ala Ala Ser Val
225                 230                 235                 240

Lys Arg Thr His Met Glu Leu Gly Gly Lys Ala Pro Val Ile Val Phe
                245                 250                 255

Asp Asp Ala Asp Ile Asp Asn Val Val Asp Gly Ile Arg Ser Phe Gly
            260                 265                 270

Phe Tyr Gln Ala Gly Asn Asp Cys Thr Ala Ala Cys Arg Leu Tyr Val
        275                 280                 285

Asn Arg Ala Val Tyr Asp Glu Val Val Glu Ala Leu Gly Lys Ala Val
    290                 295                 300

Ala Thr Leu Lys Ile Gly Asp Pro Arg Asp Glu Thr Thr Glu Leu Gly
305                 310                 315                 320

Pro Leu Ile Thr Glu Pro Asn Leu Glu Arg Val Met Gly Phe Val Glu
                325                 330                 335

Arg Ala Lys Ala Leu Pro His Ile Thr Val Val Thr Gly Gly Glu Arg
            340                 345                 350

Val Lys Gly Thr Gly Phe Tyr Phe Asn Pro Thr Val Leu Ala Gly Ala
        355                 360                 365

Lys Asn Asp Asp Glu Ile Val Asn Lys Glu Val Phe Gly Pro Val Ile
    370                 375                 380

Ser Ile Thr Ser Phe Asp Asp Glu Ala Asn Val Ile Gly Trp Ala Gln
385                 390                 395                 400

Ala Ser Gln Tyr Gly Leu Ala Ser Ser Val Trp Thr Arg Asp Ile Gly
                405                 410                 415

Arg Ala His Arg Leu Ala Ala Cys Leu Asn Tyr Gly Cys Thr Trp Val
            420                 425                 430

Gln Thr His Phe Met Leu Val Ser Glu Met Pro His Gly Gly Asn Lys
        435                 440                 445

Leu Ser Gly Tyr Gly Lys Asp Met Ser Met Tyr Gly Leu Glu Asp Tyr
    450                 455                 460

Thr Ile Val Arg His Ile Met Ile Arg His
465                 470
```

METHODS OF PRODUCING GABA

CROSS-REFERENCE TO RELATED APPLICATIONS

The present application is a continuation-in-part application of U.S. patent application Ser. No. 12/201,648 filed 29 Aug. 2008 which in turn is related to and claims priority under 35 U.S.C. §119(e) to U.S. provisional patent application Ser. No. 60/968,964 filed on 30 Aug. 2007 and to U.S. provisional patent application Ser. No. 60/986,640 filed on 9 Nov. 2007. Each application is incorporated herein by reference.

SEQUENCE SUBMISSION

The present application includes a Sequence Listing in electronic format. The Sequence Listing is entitled 3834108SequenceListingRev1.txt, was created on 13 Nov. 2012 and is 39 kb in size. The information in the electronic format of the Sequence Listing is part of the present application and is incorporated herein by reference in its entirety.

FIELD OF THE INVENTION

The present invention is in the field of recombinant production of gamma-aminobutyric acid (GABA).

BACKGROUND OF THE INVENTION

The present invention relates to methods and materials for GABA production in cells and living organisms. More particularly, the invention relates to genetic transformation of organisms, preferably plants, with genes that encode proteins that catalyze the conversion of putrescine to GABA. GABA is known to function as a neurotransmitter in animals. In plants, increased levels of GABA are associated with increased tolerance to environmental stress.

The publications and other materials used herein to illuminate the background of the invention, and in particular, cases to provide additional details respecting the practice, are incorporated by reference in their entirety for all that they disclose, and for convenience are referenced in the following text by reference number and are listed by reference number in the appended bibliography.

GABA in Response to Stress

In plants, GABA levels increase in response to a variety of stresses (1-4), but the biological significance of the rapid accumulation remains unknown (1-6). Several physiological roles for GABA synthesis in plants in response to stress have been proposed including: to maintain cytosolic pH (7, 8), to serve as an alternative store for carbon or nitrogen (N; (9), to deter insect feeding (10-12), or to serve as a signaling molecule (4-6, 13, 14).

Although the physiological role of GABA synthesis in plants in response to stress is not well defined, it has been clearly demonstrated that GABA is required for plant development and protection against biotic and abiotic stress (10-12), and that proper GABA levels, either through the regulation of biosynthesis (6, 15) or catabolism (5, 13), is required for normal plant growth and development (5, 13) and for stress survival (5). Furthermore, exogenous application of GABA results in increased plant growth and development. Elevated levels of GABA in plants may confer multiple agronomic benefits: increased plant growth and development (158, 4); increased tolerance to abiotic stresses, including drought (159), salinity (160), flooding (161), heat (162), freezing (163, 25), limited nutrient availability (164); and increased tolerance to biotic stresses, such as insect feeding (12, 165) and nematode infestation (12). GABA may function to alter nitrogen and/or carbon metabolism (1, 9, 14, 166, 167).

Metabolic Pathways that Affect GABA Accumulation in Plants

There are three known metabolic pathways that affect, or regulate, GABA levels in plants (FIG. 1). The first pathway is via the decarboxylation of glutamate by the enzyme glutamate decarboxylase (GAD or glutamic acid decarboxylase (16-18). The second pathway is via the GABA shunt (13, 19). All the components, enzymes and genes, of the two pathways have been demonstrated to exist in higher plants. A third pathway, which is associated with the catabolism of polyamines, and known to exist in bacteria, was reported over 20 years ago to exist in plant tissue (20, 21).

GABA Production by GAD

GABA accumulation in plants upon exposure to stress has been attributed to stimulation of GAD activity (1, 3, 22-25). GAD activity is controlled (23) by the binding of calcium and calmodulin to a 22-25 amino acid region at the carboxy-terminus of the protein, called a calmodulin-binding domain (26). The calmodulin-binding domain functions as an auto-inhibitory domain to deactivate the GAD enzyme (15), which is located in the cytoplasm (10, 19).

GABA Shunt

Another way to control GABA levels is by regulating the breakdown or catabolism through enzymes in the GABA shunt. GABA, synthesized in the cytoplasm by GAD, is then transported into mitochondria where it is catabolized by enzymes in the GABA shunt (19). GABA is converted into succinate semialdehyde by pyruvate-dependent GABA transaminase (GABA-T) (13, 27). Succinate semialdehyde is catabolized into succinate by succinate semialdehyde dehydrogenase (SSADH) for use in the tricarboxylic acid (TCA) cycle (5, 28, 29). Succinate semialdehyde can also be converted into gamma-hydroxybutyrate by gamma-hydroxybutyrate dehydrogenase (30).

GABA Production Through Polyamine Catabolism

The catabolism of polyamines into GABA has been documented in plants (20), and the genes and corresponding enzymes have been identified (reviewed in [A. Cona, G. Rea, R. Angelini, R. Federico, P. Tavladoraki, Trends in Plant Science 11, 80 (2006)]). Putrescine is converted into GABA through a two-step enzymatic reaction. DAO catalyzes the oxidation of putrescine into gamma-aminobutyricaldehyde, hydrogen peroxide, and ammonium. Gamma-aminobutyricaldehyde spontaneously converts into $\Delta^1$-pyrroline. Pyrroline dehydrogenase (PDH) oxidizes $\Delta^1$-pyrroline to form GABA. Spermidine is also converted into GABA via PAO to form gamma-aminobutyricaldehyde, which spontaneously converts into $\Delta^1$-pyrroline and is converted to GABA by PDH. In bacteria, the catabolism of polyamines into GABA is well documented, and the genes and encoded enzymes have been identified (31, 32). In E. coli, putrescine can be converted into GABA through a two-step enzymatic reaction. An amino group from putrescine is transferred to alpha-ketoglutarate to form gamma-aminobutyricaldehyde and glutamate by putrescine aminotransferase (PAT) (33). Oxidation of gamma-aminobutyricaldehyde by gamma-aminobutyricaldehyde dehydrogenase (GABAlde DeHase) forms GABA (34). Although the polyamine catabolic pathway that forms GABA has been reported in plant tissues (20, 21), there are no reports of the PAT activity in plants, suggesting that plants do not utilize the "bacterial putrescine catabolic" pathway.

SUMMARY OF THE INVENTION

The present invention relates to methods and compositions for regulating GABA production in organisms. More particularly, GABA production in organisms is regulated through the use of polynucleotides that encode a functional putrescine aminotransferase (PAT) gene product (also sometimes simply referred to as "PAT" herein) and/or a functional gamma-aminobutyricaldehyde dehydrogenase (GABAlde DeHase) gene product (also sometimes simply referred to as "GABAlde DeHase" herein) in plants. The present invention provides methods for transforming plants, constructing vector constructs and other nucleic acid molecules for use therein. The transformed plants have the advantage of enhanced GABA production.

Thus, in one aspect, the present invention provides polynucleotides encoding functional PAT and/or GABAlde DeHase. In one embodiment, two expression units are provided. The first expression unit comprises a first promoter operably linked to a first polynucleotide which encodes PAT. The second expression unit comprises a second promoter operably linked to a second polynucleotide which encodes GABAlde DeHase. In a second embodiment, a single expression unit is provided. In one aspect, the single expression unit comprises a third promoter operably linked to a third polynucleotide which encodes PAT. In another aspect, the single expression unit comprises third promoter operably linked to a third polynucleotide which encodes PAT and GABAlde DeHase. In one embodiment, PAT is encoded by a polynucleotide comprising a nucleotide sequence set forth in SEQ ID NO:1, SEQ ID NO:44, SEQ ID NO:45, SEQ ID NO:46, SEQ ID NO:47 or SEQ ID NO:48. In another embodiment, GABAlde DeHase is encoded by a polynucleotide comprising a nucleotide sequence set forth in SEQ ID NO:3, SEQ ID NO:49 or SEQ ID NO:50. In an additional embodiment, the present invention provides cells comprising these polynucleotides.

In accordance with this aspect of the invention, these polynucleotides are used to transform plant cells or to transform plants to produce transgenic plant cells and/or plants. The transgenic plants have advantages of enhanced GABA production, that result in enhanced plant growth characteristics (such as root mass, biomass or yield), survival characteristics and/or tolerance to environmental (such as drought or elevated temperature) or other plant stresses (such as insect or nematode feeding), without causing stunting or other deleterious morphological alterations. Plants are genetically modified in accordance with the invention to introduce into the plant a polynucleotide that encodes PAT and/or a polynucleotide that encodes a GABAlde DeHase, which function in the formation of GABA in the plant.

In a second aspect, the present invention provides the production of GABA in cells or organisms using polynucleotides that encode functional PAT and/or polynucleotides that encode functional GABAlde DeHase that are expressed in the cells or organisms. In one embodiment, the organism is a eukaryote. In another embodiment, the organism is a prokaryote. In an additional embodiment, the cell is a eukaryotic cell. In a further embodiment, the cell is a prokaryotic cell.

DETAILED DESCRIPTION OF THE INVENTION

Figure 1:
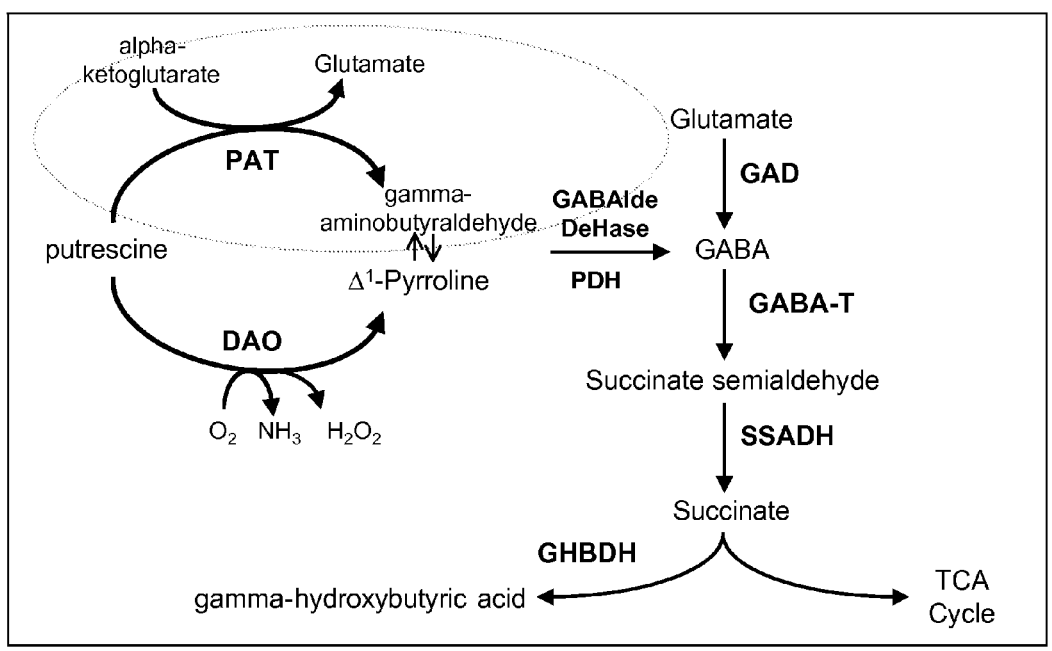
FIG. 1 shows GABA biosynthetic and catabolic pathways. GABA is produced from glutamate by the enzyme glutamate decarboxylase (GAD). GABA is converted into succinate semialdehyde by the enzyme pyruvate-dependent GABA transaminase (GABA-T). Succinate semialdehyde is converted into succinate by the enzyme succinate semialdehyde dehydrogenase (SSADH) for use in the tricarboxylic acid (TCA) cycle. Succinate semialdehyde can also be converted into gamma-hydroxybutyrate by the enzyme gamma-hydroxybutyrate dehydrogenase (GHBDH). GABA can also be produced from putrescine through a two-step enzymatic reaction. DAO catalyzes the oxidation of putrescine into gamma-aminobutyricaldehyde, hydrogen peroxide, and ammonium. Gamma-aminobutyricaldehyde spontaneously converts into $\Delta^1$-pyrroline. Pyrroline dehydrogenase (PDH) oxidizes $\Delta^1$-pyrroline to form GABA. In bacteria putrescine can be converted into GABA also through a two-step enzymatic reaction (highlighted by the gray oval). An amino group from putrescine is transferred to alpha-ketoglutarate to form gamma-aminobutyricaldehyde and glutamate by the enzyme putrescine aminotransferase (PAT). Oxidation of gamma-aminobutyricaldehyde by enzyme gamma-aminobutyricaldehyde dehydrogenase (GABAlde DeHase) forms GABA.

The present invention describes the methods for the synthesis of DNA constructs for GABA production from polynucleotides and vectors and the methods for making transformed organisms including plants, photosynthetic organisms, microbes, invertebrates, and vertebrates. The present invention is unique in that it describes an alternative approach to increase GABA production, namely by the insertion of the bacterial putrescine catabolic pathway, in organisms where the pathway does not exist or has not clearly been identified. The invention describes methods for the use of polynucleotides that encode functional putrescine aminotransferase (PAT) and/or gamma-aminobutyricaldehyde dehydrogenase (GABAlde DeHase) in plants to increase GABA production. The preferred embodiment of the invention is in plants but other organisms may be used.

One embodiment of the invention is a method for the production of GABA by the following steps:

1. operably link a promoter to the 5' end of the polynucleotide for a functional PAT gene product;
2. insert the polynucleotide construct (from step 1 above) into a vector;
3. transform the vector containing the PAT construct into a plant or plant cell;
4. operably link a promoter to the 5' end of the polynucleotide for the functional GABAlde DeHase gene product;
5. insert the polynucleotide construct (from step 4 above) into a vector; and
6. transform the vector containing the GABAlde DeHase construct into a plant or plant cell carrying a PAT construct or one that expresses a functional PAT gene product.

Another embodiment of the invention is a method for the production of GABA by the following steps:

1. operably link a promoter to the 5' end of the polynucleotide for the functional PAT gene product;
2. insert the polynucleotide construct (from step 1 above) into a vector;
3. transform the vector containing the PAT construct into a plant or plant cell;
4. operably link a promoter to the 5' end of the polynucleotide for the functional GABAlde DeHase gene product;
5. insert the polynucleotide construct (from step 4 above) into a vector;
6. transform the vector containing the GABAlde DeHase construct into a plant or plant cell; and 7. Sexually cross a plant (or fuse cells) carrying a PAT construct or one that expresses a functional PAT with a plant (or cells) carrying a GABAlde DeHase construct or one that expresses a functional GABAlde DeHase.

Another embodiment of the invention is a method for the production of GABA by the following steps:

1. In the same vector, operably link a promoter to the 5' end of the polynucleotide for the functional PAT gene product;
2. operably link a promoter to the 5' end of the polynucleotide for the functional GABAlde DeHase gene product;
3. insert the two polynucleotides into the vector in such a manner that both polynucleotides are expressed by one promoter or each polynucleotide is expressed by one promoter; and
4. transform the vector containing the PAT and GABAlde DeHase construct into a plant or plant cell.

Another embodiment of the invention is a method for the production of GABA by the following steps:

1. operably link a promoter to the 5' end of the polynucleotide for a functional PAT gene product; and
2. insert the polynucleotide construct (from step 1 above) into a vector; transform the vector containing the PAT construct into a plant or plant cell.

Another embodiment of the invention is a polynucleotide that encodes a functional PAT and a polynucleotide that encodes a functional GABAlde DeHase can be cloned into a suitable vector for transformation in microbes, photosynthetic organisms, insects, invertebrate or vertebrates or their cells.

Suitable Polynucleotides for PAT and GABAlde DeHase

A suitable polynucleotide for PAT is provided in SEQ ID NO:1, SEQ ID NO:44, SEQ ID NO:45, SEQ ID NO:46, SEQ ID NO:47 or SEQ ID NO:48. Other suitable polynucleotides for use in accordance with the invention may be obtained by the identification of polynucleotides that selectively hybridize to the polynucleotides of SEQ ID NO:1, SEQ ID NO:44, SEQ ID NO:45, SEQ ID NO:46, SEQ ID NO:47 or SEQ ID NO:48 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1 when it used as a reference for sequence comparison or polynucleotides that encode polypeptides that have substantial identity to amino acid sequence of SEQ ID NO:2 when it used as a reference for sequence comparison.

A suitable polynucleotide for GABAlde DeHase is provided in SEQ ID NO:3, SEQ ID NO:49 or SEQ ID NO:50. Other suitable polynucleotides for use in accordance with the invention may be obtained by the identification of polynucleotides that selectively hybridize to the polynucleotides of SEQ ID NO:3, SEQ ID NO:49 or SEQ ID NO:50 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:3 when it used as a reference for sequence comparison or polynucleotides that encode polypeptides that have substantial identity to amino acid sequence of SEQ ID NO:4 when it is used as a reference for sequence comparison.

Variability and Modification of the Sequences of the Desired Invention

Those of ordinary skill in the art know that organisms of a wide variety of species commonly express and utilize homologous proteins, which include the insertions, substitutions and/or deletions discussed above, and effectively provide similar function. For example, the amino acid sequences for PAT or GABAlde DeHase from E. coli may differ to a certain degree from the amino acid sequences of PAT or GABAlde DeHase in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

Another embodiment of the invention is a polynucleotide (e.g., a DNA construct) that encodes a protein that functions as a PAT and selectively hybridizes to either SEQ ID NO:1, SEQ ID NO:44, SEQ ID NO:45, SEQ ID NO:46, SEQ ID NO:47 or SEQ ID NO:48 or encodes a protein that functions as a GABAlde DeHase and selectively hybridizes to either SEQ ID NO:3, SEQ ID NO:49 or SEQ ID NO:50. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:2 or SEQ ID NO:4 or the polypeptides encoded by SEQ ID NO:44, SEQ ID NO:45, SEQ ID NO:46, SEQ ID NO:47 or the polypeptides encoded by SEQ ID NO:48 or by SEQ ID NO:49 or SEQ ID NO:50. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, PAT or GABAlde DeHase activity is generally at least 40%, 50%, 60%, 70%, 80% or 90%, preferably 60-90% of the native protein for the native substrate. Tables of conserved substitution provide lists of functionally similar amino acids.

The following three groups each contain amino acids that are conserved substitutions for one another: (1) Alanine (A), Serine (S), Threonine (T); (2) Aspartic acid (D), Glutamic acid (E); and (3) Asparagine (N), Glutamine (Q);

For example, it is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in both monocotyledonous and dicotyledonous plant species, sequences can be modified to account for the specific codon preferences and GC-content preferences of monocotyledonous plants or dicotyledonous plants, as these preferences have been shown to differ (41).

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art (42-49).

A suitable polynucleotide for use in accordance with the invention may be obtained by cloning techniques using cDNA or genomic libraries, DNA, or cDNA from bacteria which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using fusion-(156) or overlap-PCR (157) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are ligated together by recombination.

The recombinant expression cassette or DNA construct includes a promoter that directs transcription in a plant cell, operably linked to the polynucleotide encoding a PAT or a GABAlde DeHase. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Promoters

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter is induced by one or more, but not limiting to one of the following, abiotic stresses such as wounding, cold, dessication, ultraviolet-B (50), heat shock (51) or other heat stress, drought stress or water stress. The promoter may further be one induced by biotic stresses including pathogen stress, such as stress induced by a virus (52) or fungi (53, 54), stresses induced as part of the plant defense pathway (55) or by other environmental signals, such as light (56), carbon dioxide (57, 58), hormones or other signaling molecules such as auxin, hydrogen peroxide and salicylic acid (59, 60), sugars and gibberellin (61) or abscissic acid and ethylene (62).

In other embodiments of the invention, tissue-specific promoters are used. Tissue-specific expression patterns as controlled by tissue- or stage-specific promoters that include, but is not limited to, fiber-specific, green tissue-specific, root-specific, stem-specific, and flower-specific. Examples of the utilization of tissue-specific expression includes, but is not limit to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Although many promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphenol carboxylase gene (63). There are suitable promoters for root specific expression (64, 65). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV). The promoter may further be, for example, a promoter for the small subunit of ribulose-1,3-biphosphate carboxylase. Promoters of bacterial origin include the octopine synthase promoter, the nopaline synthase promoter and other promoters derived from native Ti plasmids could also be (66).

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

In another embodiment of the invention, a DNA construct comprising a plant GAD promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate decarboxylase. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). For example, the full-length promoter for the nodule-enhanced PEP carboxylase from alfalfa is 1277 basepairs prior to the start codon (67), the full-length promoter for cytokinin oxidase from orchid is 2189 basepairs prior to the start codon (68), the full-length promoter for ACC oxidase from peach is 2919 basepairs prior to the start codon (69), full-length promoter for cytokinin oxidase from orchid is 2189 basepairs prior to the start codon, full-length promoter for glutathione peroxidase1 from *Citrus sinensis* is 1600 basepairs prior to the start codon (70), and the full-length promoter for glucuronosyltransferase from cotton is 1647 basepairs prior to the start codon (71). Most full-length promoters are 1700 basepairs prior to the start codon. The accepted convention is to describe this region (promoter) as −1700 to −1, where the numbers designate the number of basepairs prior to the "A" in the start codon. In this embodiment of the invention that the region of −2000 to −1 basepairs 5' to a plant GAD is operably linked to a polynucleotide for the said encoded peptide to make a transformed plant that selectively expresses the polynucleotide or increases the level of the said protein where the plant GAD is expressed or accumulates. A plant GAD promoter is the −2000 to −1 basepair region genes that include, but is not limit to, the 5 *Arabidopsis thaliana* GADs (AtGAD) (22), petunia GAD (26), tomato GAD (72), tobacco GAD (73), rice (74), barely, poplar, soybean, mustard, orange, *Medicago truncatula*, grape and pine. Those of ordinary skill in the art can either digest the desired region using restriction enzymes and ligase to clone the plant GAD promoters or use amplification, such as PCR, techniques with the incorporation of restriction or recombination sites to clone the plant GAD promoters 5' to the desired polynucleotide. A plant GAD promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

Suitable Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (66, 75) and numerous expression cassettes and vectors and in vitro culture methods for plant cell or tissue transformation and regeneration of plants are known and available (76). The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, microbes, invertebrates or vertebrates.

It is known by those of ordinary skill in the art that there exist numerous expression systems available for expression of a nucleic acid encoding a protein of the present invention. There are many commercially available recombinant vectors to transform a host plant or plant cell. Standard molecular and cloning techniques (46, 49, 77) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, such as ubiquitin, to direct transcription, a ribosome-binding site for translational initiation, and a transcription/translation terminator.

One of ordinary skill to the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs requires an appropriate transcriptional terminator to be attached downstream of the desired gene of the invention for proper expression in plants. Several such terminators are available and known to persons of ordinary skill in the art. These include, but are not limited to, the tml from CaMV and E9 from rbcS. Another example of a terminator sequence is the polyadenlyation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. An example of specific polyadenylation sequence in higher eukaryotes is ATTTA. Examples of plant polyadenylation signal sequences are AATAAA or AATAAT. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA (78, 79).

In addition, polynucleotides that encode a PAT or a GABAlde DeHase can be placed in the appropriate plant expression vector used to transform plant cells. The polypeptide can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional PAT or GABAlde DeHase to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence to direct the desired polypeptide in the host cell, so that the polypeptide accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (80-83), C-terminus (84, 85) or internal (86-88) or tertiary structure (88). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (89, 90), iPSORT (91), SignalP (92), PrediSi (93), ELSpred (94) HSLpred (95) and PSLpred (96), MultiLoc (97), SherLoc (98), ChloroP (99), MITOPROT (100), Predotar (101) and 3D-PSSM (102). Additional methods and protocols are discussed in the literature (97).

Transformation of Host Cells

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (103).

Those of ordinary skill in the art can use different plant gene transfer techniques found in references for, but not limited to, the electroporation (104-108), microinjection (109, 110), lipofection (111), liposome or spheroplast fusions (112-114), *Agrobacterium* (115), direct gene transfer (116), T-DNA mediated transformation of monocots (117), T-DNA mediated transformation of dicots); (118, 119), microprojectile bombardment or ballistic particle acceleration (120-123), chemical transfection including $CaCl_2$ precipitation, polyvinyl alcohol, or poly-L-ornithine (124), silicon carbide whisker methods (125, 126), laser methods (127, 128), sonication methods (129-131), polyethylene glycol methods (132), vacuum infiltration (133), and transbacter (155)

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include microbes, invertebrate, vertebrates or photosynthetic organisms. Preferred host cells are eukaryotic, preferably plant cells, such as those derived from monocotyledons, such as duckweed, corn, rye grass, Bermuda grass, Blue grass, Fescue, or dicotyledons, including lettuce, cereals such as wheat, rapeseed, radishes and cabbage, green peppers, potatoes and tomatoes, and legumes such as soybeans and bush beans.

Suitable Plants

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, aneth, apple, apricot, artichoke, arugula, asparagus, avocado, banana, barley, beans, beech, beet, Bermuda grass, blackberry, blueberry, Blue grass, broccoli, Brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include bacteria, fungi, algae and other photosynthetic organisms, and animals including vertebrate and invertebrates.

Once transformed, the plant may be treated with other "active agents" either prior to or during the exposure of the plant to stress to further decrease the effects of plant stress. "Active agent," as used herein, refers to an agent that has a beneficial effect on the plant or increases production of amino acid production by the plant. For example, the agent may have a beneficial effect on the plant with respect to nutrition, and the resistance against, or reduction of, the effects of plant stress. Some of these agents may be precursors of end products for reaction catalyzed by PAT or GABAlde DeHase. These compounds could promote growth, development, biomass and yield, and change in metabolism. In addition to the twenty amino acids that are involved in protein synthesis, other non-protein amino acids, such as GABA, citrulline, and ornithine, or other nitrogen containing compounds such as polyamines may also be used to activate PAT or GABAlde DeHase. Depending on the type of gene construct or recombinant expression cassette, other metabolites and nutrients may be used to activate PAT or GABAlde DeHase. These include, but are not limited to, sugars, carbohydrates, lipids, oligopeptides, mono-(glucose, arabinose, fructose, xylose, and ribose) di-(sucrose and trehalose) and polysaccharides, carboxylic acids (succinate, malate and fumarate) and nutrients such as phosphate, molybdate, or iron.

Accordingly, the active agent may include a wide variety of fertilizers, pesticides and herbicides known to those of ordinary skill in the art (134). Other greening agents fall within the definition of "active agent" as well, including minerals such as calcium, magnesium and iron. The pesticides protect the plant from pests or disease and may be either chemical or biological and include fungicides, bactericides, insecticides and anti-viral agents as known to those of ordinary skill in the art.

Expression in Prokaryotes

The use of prokaryotes as hosts includes strains of E. coli. However, other microbial strains including, but not limited to, Bacillus (135) and Salmonella may also be used. Commonly used prokaryotic control sequences include promoters for transcription initiation, optionally with an operator, along with ribosome binding site sequences. Commonly used prokaryotic promoters include the beta lactamase (136), lactose (136), and tryptophan (137) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art.

Expression in Non-Plant Eukaryotes

The present invention can be expressed in a variety of eukaryotic expression systems such as yeast, insect cell lines, and mammalian cells which are known to those of ordinary skill in the art. For each host system there are suitable vectors that are commercially available (e.g., Invitrogen, Startagene, GE Healthcare Life Sciences). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins in yeast is well known to those of ordinary skill in the art (138, 139). The most widely used yeasts are Saccharomyces cerevisiae and Pichia pastoris. Insect cell lines that include, but are not limited to, mosquito larvae, silkworm, armyworm, moth, and Drosophila cell lines can be used to express proteins of the present invention using baculovirus-derived vectors. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines.

A protein of the present invention, once expressed in any of the non-plant eukaryotic systems can be isolated from the organism by lysing the cells and applying standard protein isolation techniques to the lysates or the pellets. The monitoring of the purification process can be accomplished by using western blot techniques or radioimmunoassay of other standard immunoassay techniques.

DEFINITIONS

Unless defined otherwise, all technical and scientific terms used herein have the same meaning as is commonly understood by one of skill in the art to which the invention belongs.

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription.

The term "plant promoter" refers to a promoter capable of initiating transcription in plant cells.

The term "animal promoter" refers to a promoter capable of initiating transcription in animal cells.

The term "microbe promoter" refers to a promoter capable of initiating transcription in microbes.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "constitutive" refers to a promoter that is active under most environmental and developmental conditions, such as, for example, but not limited to, the CaMV 35S promoter and the nopaline synthase terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "inducible promoter" refers to a promoter that is under environmental control.

The terms "encoding" and "coding" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers Amino acids may be referred to by their commonly known three-letter or one-letter symbols Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The terms "putrescine aminotransferase" and "PAT" refer to the protein (EC 2.6.1.82) that catalyzes the following reactions:

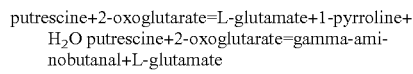

NOTE: 1-Pyrroline forms spontaneously from gamma-aminobutanal.

NOTE: 2-oxoglutarate is another name for alpha-ketoglutarate.

Other names for PAT include: putrescine: alpha-ketoglutarate transaminase, putrescine: alpha-ketoglutarate aminotransferase, YgjG, putrescine:2-oxoglutarate aminotransferase, putrescine:2-ketoglutarate transaminase putrescine transaminase. Other names for PAT include: putrescine: alpha-ketoglutarate transaminase, putrescine: alpha-ketoglutarate aminotransferase, YgjG, putrescine:2-oxoglutarate aminotransferase, putrescine:2-ketoglutarate transaminase putrescine transaminase.

The terms "gamma-aminobutyricaldehyde dehydrogenase" and "GABAlde DeHase" refer to the protein (EC 2.6.1.82) that catalyzes the following reaction: The terms "gamma-aminobutyricaldehyde dehydrogenase" and "GABAlde DeHase" refer to the protein (EC 2.6.1.82) that catalyzes the following reaction:

Other names for GABAlde DeHase include: 1-pyrroline dehydrogenase, ABALDH, YdcW, aminobutyricaldehyde dehydrogenase, gamma-guanidinobutyraldehyde dehydrogenase, ABAL dehydrogenase, 4-aminobutyricaldehyde dehydrogenase, 4-aminobutanal dehydrogenase, gamma-aminobutyricaldehyde dehydroganase, gamma-guanidinobutyraldehyde dehydrogenase.

The term "functional" with reference to PAT or GABAlde DeHase refers to peptides, proteins or enzymes that catalyze the PAT or GABAlde DeHase reactions, respectively.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (140), where the $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature (77, 141) Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT, (142) can perform an optimal alignment of sequences for comparison using a homology alignment algorithm called GAP (143), search for similarity using Tfasta and Fasta (144), by computerized implementations of these algorithms widely available on-line or from various vendors (Intelligenetics, Genetics Computer Group). CLUSTAL allows for the alignment of multiple sequences (145-147) and program PileUp can be used for optimal global alignment of multiple sequences (148). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (143) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (149).

Unless otherwise stated, sequence identity or similarity values refer to the value obtained using the BLAST 2.0 suite of programs using default parameters (150). As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (151, 152) and XNU (153).

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch (154), thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (143). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.);

*Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Development of a Transgenic Plant that Constitutively Expresses Pat and GABAlde DeHase Using a Sexual Cross Step 1: Make a DNA construct that contains an AtTUB5 (locus tag At1g20010) promoter with a PAT gene and a NOS terminator in the following manner.

Step 1a. Use PCR to amplify the AtTUB5 promoter (−1851 to −1 bps) using 500 ng of DNA from an *Arabidopsis thaliana* Col-0 lambda genomic library. Add 500 ng of the following primers: 5'KpnTUB5prom (5'-ttttGGTACCcacatttgcaaaatgatgaatg-3'; SEQ ID NO:5) and 3'BamTUB5prom (5'-ttttGGATCCccaatctggttaccgcattgac-3'; SEQ ID NO:6); in this and subsequent examples the capitalized nucleotides are restriction enzyme sites introduced into the primer during its synthesis. Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with BamHI. Inactivate the restriction enzyme as described by the manufacturer.

Step 1b. Use PCR to amplify the PAT using 500 ng of DNA from *E. coli* strain K12. Add 500 ng of the following primers: 5'BamPAT (5'-ttttGGATCCatgttgaacaggttaccttcga-3'; SEQ ID NO:7) and 3'XbaPAT (5'-ttttTCTAGAttacgcttatcgacacttact-3'; SEQ ID NO:8). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with BamHI and XbaI. Inactivate the restriction enzyme as described by the manufacturer.

Step 1c. Use PCR to amplify the NOS terminator using 500 ng of pPV1. Add 500 ng of the following primers: 5'XbaNOSterm (5'-ttttTCTAGAtaccgagctcgaatttccccga-3'; SEQ ID NO:9) and 3'PstNOSterm (5'-ttttCTGCAGgatctagtaacatagatgacac-3'; SEQ ID NO:10). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with XbaI. Inactivate the restriction enzyme as described by manufacturer.

Step 1d. Combine the digested fragments (from steps 1a, 1b, and 1c) and ligate at 4° C. overnight. Use the ligated fragment as a template for PCR to amplify the entire construct by adding 500 ng of the following primers: 5'KpnTUB5prom and 3'Pst-NOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with KpnI and PstI and ligate into vector pCAMBIA1105.1 that has been predigested with KpnI and PstI.

Step 1e. Transform the ligated vector containing the DNA construct by electroporation into *E. coli*. Select for spectinomycin (100 µg/ml) or streptomycin (200 µg/ml) resistance on LB plates. Confirm the presence of the DNA constructs in the selected colonies by PCR analysis with the 5'KpnTUB5prom and 3'PstNOSterm primers using the following program: 96° C. for 3 min followed by 25 cycles of 94° C. for 30 seconds, 55° C. for 30 seconds, 72° C. for 5 min, and 72° C. for 3 min. Grow a colony that contains the proper DNA construct overnight at 37° C. in 6 ml LB plus spectinomycin (100 µg/ml) or streptomycin (200 µg/ml). Isolate the plasmid DNA that contains the DNA construct by Wizard Plus SV Minipreps DNA Purification System (Promega Corporation, Madison, Wis., USA). Sequence the DNA insert to confirm its identity and the fidelity of the DNA construct.

Step 2: Make a DNA construct that contains an AtTUB5 promoter with a GABAlde DeHase gene and a NOS terminator in the following manner.

Step 2a. Use the AtTUB5 promoter (−1851 to −1 bps) that was amplified in Step 1a.

Step 2b. Use PCR to amplify the GABAlde DeHase using 500 ng of DNA from *E. coli* strain K12. Add 500 ng of the following primers: 5'BamGABAlde DeHase (5'-ttttGAGCTCatgcaacataagttactgatta-3'; SEQ ID NO:11) and 3'XbaGABAlde DeHase (5'-ttttTCTAGAttaat gtttaaccatgacgtgg-3'; SEQ ID NO:12). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with BamHI and XbaI. Inactivate the restriction enzyme as described by manufacturer.

Step 2c. Use the NOS terminator that was amplified that was amplified in Step 1c.

Step 2d. Combine the digested fragments (from steps 2a, 2b, and 2c) and ligate at 4° C. overnight. Use the ligated fragment as a template for PCR to amplify the entire construct fragment by adding 500 ng of the following primers: 5'KpnTUB5prom and 3'Pst-NOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with KpnI and PstI and ligate into the vector pCAMBIA2301 that has been predigested with KpnI and PstI.

Step 2e. Transform the ligated vector containing the DNA construct by electroporation into *E. coli*. Confirm the transformation of the DNA constructs, purify the plasmid DNA containing the DNA construct to confirm its identity and the fidelity of the sequence as described in Step 1e above.

Step 3: Transform *Agrobacterium tumefaciens*

Independently transform each vector construct into electrocompetent *Agrobacterium tumefaciens* EHA105, as described by the Green Lab Protocol (http colon//www dot bch dot msu dot edu/pamgreen/green dot htm). Select positive transformants using Terrific Broth plus spectinomycin (100 μg/ml) or streptomycin (200 μg/ml) on 1% agar plates. Confirm *Agrobacterium* colonies by PCR using the following primers: 5'KpnTUB5prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min.

Step 4: Transform Plant, *Arabidopsis thaliana*

Step 4a: Sow *Arabidopsis* (L.) Heynh. ecotype Columbia (Col-0) seeds in 248 cm² plastic pots with moistened soil (Promix HP, Premier Horticulture Inc., Redhill, Pa., Canada). Grow plants at 20-21° C., with 60-70% relative humidity, under cool white fluorescent lights (140 umol m$^{-2}$ s$^{-1}$) with a 16 h light/8 h dark cycle. Water plants as needed by subirrigation. After two weeks, transfer five individual plants to smaller pots (72 cm²) for use in the transformation protocol. Grow the plants until the first floral buds and flowers form (2-3 additional weeks).

Step 4b: Independently grow a *Agrobacterium* colony for each construct to be transformed, in 500 ml of Terrific Broth plus spectinomycin (100 μg/ml) or streptomycin (200 μg/ml) for 2-3 days at 29° C. Collect cells by centrifugation at 6000 rpm for 15 minutes, and resuspend cells in 5% sucrose plus 0.05% surfactant (Silwet L-77, Lehle Seeds, Round Rock, Tex., USA) solution.

Step 4c: Transform plants by the floral dip transformation (Bechtold et al., Methods Mol Biol 82, 259, 1998). Keep the plants in sealed containers to maintain high humidity for 16 to 24 h and maintain plants as described in step 4a above. At 8 to 10 weeks, dry the plants, collect the seeds, and select for the marker in each line. Select for hygromycin resistance for the TUB5::PAT constructs in pCAMBIA1105.1 by incubating seeds on plates containing 4.418 g/L Murashige and Skoog Salt and Vitamin Mixture (MS medium, Life Technologies, Grand Island, N.Y., USA) plus hygromycin (50 μg/ml) and 0.8% (wt vol) Phytagar. Select for kanamycin resistance for the TUB5::GABAlde DeHase constructs in pCAMBIA2301 by incubating seeds on plates containing 4.418 g/L Murashige and Skoog Salt and Vitamin Mixture (MS medium, Life Technologies, Grand Island, N.Y., USA) plus kanamycin (50 μg/ml) and 0.8% (wt vol) Phytagar. Collect and transfer positively selected plants into pots containing soil and grow for 5 to 6 weeks. Allow the plants to self-pollinate. Collect the seeds and repeat the selection process until homozygotes are identified. Once homozygotes are identified and confirmed by PCR, sexually cross the two lines. After 3 to 4 weeks, collect the seeds and select for hygromycin and kanamycin resistance by plating seeds on plates containing 4.418 g/L Murashige and Skoog Salt and Vitamin Mixture (MS medium, Life Technologies, Grand Island, N.Y., USA) plus hygromycin (50 μg/ml), kanamycin (50 mg/ml) and 0.8% (wt/vol) Phytagar.

EXAMPLE 2

Development of a Transgenic Plant that Non-Constitutively Expresses (Using an AtGAD2 Promoter) PAT and GABAlde DeHase Using a Sexual Cross Step 1: Make a DNA construct that contains an AtGAD2 (locus tag At1g65960) promoter with a PAT gene and a NOS terminator in the following manner.

Step 1a: Use PCR to amplify the AtGAD2 promoter (−1714 to −1 bps) using 500 ng of DNA from an *Arabidopsis thaliana* Col-0 lambda genomic library. Add 500 ng of the following primers: 5'KpnAtGAD2prom (5'-ttttGGTAC-CTCTTACCTTGTCC TGCAACGAG-3'; SEQ ID NO:13) and 3' SacAtGAD2prom (5'-ttttGAGCTCCTTTGTTTCTGT TTAGTGAAAG-3'; SEQ ID NO:14). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI. Inactive the restriction enzyme.

Step 1b: Use PCR to amplify the PAT gene from 500 ng of DNA from *E. coli* strain K12. Add 500 ng of the following primers: 5' SacPAT (5'-ttttGAGCTCatgttgaacaggttaccttcga-3'; SEQ ID NO:15) and 3'XbaPAT (5'-ttttTCTAGAttacgcttct-tcgacacttact-3'; SEQ ID NO:16). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI and XbaI. Inactivate the restriction enzyme.

Step 1c: Use PCR to amplify the NOS terminator and digest the resulting DNA fragment with XbaI as in Example 1: step 1c.

Step 1d: Combine the digested fragments (as in Example 2: 1a, 1b, and 1c) and ligate at 4° C. overnight. Use the ligated fragment as a template for PCR to amplify the entire construct by adding 500 ng of the following primers: 5'KpnAtGAD2prom and 3'Pst-NOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with KpnI and PstI and ligate into the vector pCAMBIA1105.1 that has been predigested with KpnI and PstI.

Step 1e: Transform *E. coli*, select for antibiotic resistance, conduct PCR identification of cloned DNA constructs in transformants, purify DNA and sequence as in Example 1: step 1e.

Step 2: Make a DNA construct that contains an AtGAD2 promoter with a GABAlde DeHase gene and a NOS terminator to in the following manner.

Step 2a: Use the AtGAD2 promoter (−1714 to −1 bps) that was amplified in Example 2: Step 1a above.

Step 2b: Use PCR to amplify the GABAlde DeHase using 500 ng of DNA from *E. coli* strain K12. Add 500 ng of the following primers: 5'SacGABAlde DeHase (5'-ttttGAGCTC atgcaacataagttactgatta-3'; SEQ ID NO:17) and 3'XbaGABAlde DeHase (5'-ttttTCTAGAttaatgttt aaccat-gacgtgg-3'; SEQ ID NO:18). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI and XbaI. Inactive the restriction enzyme.

Step 2c: Use the NOS terminator that was amplified in Example 2: Step 1c.

Step 2d: Combine the digested fragments (from Example 2: 2a, 2b, and 2c) and ligate at 4° C. overnight. Use the ligated fragment as a template for PCR to amplify the entire construct by adding 500 ng of the following primers: 5'KpnAtGAD2prom and 3'Pst-NOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with KpnI and PstI and ligate into the vector pCAMBIA2301 that has been digested with KpnI and PstI.

Step 2e: Transform ligated vector and gene cassette by electroporation, confirm the identity of transformed colonies, purify the plasmid that contains the DNA construct to confirm its identity and the fidelity of the sequence as described in Example 1: step 1e.

Step 3: Transform *Agrobacterium tumefaciens*: Independently transform each DNA construct into *Agrobacterium tumefaciens*, select for antibiotic resistance and confirm the presence of the DNA construct as described in Example 1: Step 3.

Step 4: Transform plant, *Arabidopsis thaliana*: Independently transform each gene construct into *Arabidopsis thaliana*, select for antibiotic resistance, select for homozygote plants, sexually cross the two lines, and confirm the presence of the DNA constructs as described in Example 1: Step 4.

EXAMPLE 3

Development of a Transgenic Plant that Non-Constitutively Expresses (AtGAD1 Promoter) PAT and GABAlde DeHase Using Fusion PCR Step 1: Make a DNA construct that contains an AtGAD1 (locus tag At5g17330) promoter with a PAT gene and a NOS terminator in the following manner.

Step 1a: Use PCR to amplify the AtGAD1 promoter (−1732 to −1 bps) with a short overlap for the 5' end of PAT at the 3' end of the promoter using 500 ng of genomic DNA isolated from an *Arabidopsis thaliana* Col-0. Add 300 nM of the following primers: AP1 (5'-Tttt GGTACCaccaaaggatac-cctgatttg-3'; SEQ ID NO:19) and AP3 (5'-cgctcgaaggtaacct-gttcatcacgg agatgagagagagag-3'; SEQ ID NO:20). Run the PCR as described in (156).

Step 1b: Use PCR to amplify the PAT gene from 500 ng of DNA from *E. coli* strain K12. Add 300 nM of the following primers: 5'PAT (5'-atgaacaggttaccttcgagcg-3'; SEQ ID NO:21) and 3'PAT (5'-ttacgcttcttcgacacttact-3'; SEQ ID NO:22). Run the PCR exactly as described in (156).

Step 1c: Use PCR to amplify the NOS terminator with a short overlap for the 3' end of PAT at the 5' end of the terminator using 500 ng of pPV1. Add 300 nM of the following primers AP4 (5'-agtaagtgtcgaagaagcgtaa gctaccgagctcgaatttcc-3'; SEQ ID NO:23) and AP6 (5'-ttttTCTA GAaacgacggccagtgaattccc-3'; SEQ ID NO:24). Run the PCR as described in (156).

Step 1d: Combine the amplified fragments from Example 3: steps 1a, 1b, and 1c and 300 nM of the following primers AP2 (5'-ttttttttGGTACCgatatttgagcaaaactgtgg-3'; SEQ ID NO:25) and AP5 (5'-ttttttttftTCTAGAgatctagtaacatagatgacac-3'; SEQ ID NO:26). Run the PCR as described in (156). Clone the amplified DNA fragment into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAM-BIA1300 that has been predigested with Acc65I and XbaI.

Step 2: Make a DNA construct that contains an AtGAD1 promoter with a GABAlde DeHase gene and a NOS terminator to in the following manner.

Step 2a: Use PCR to amplify the AtGAD1 promoter (−1732 to −1 bps) with a short overlap of the 5' end of GABAlde DeHase at the 3'-end of GABAlde DeHase using 500 ng of genomic DNA isolated from an *Arabidopsis thaliana* Col-0. Add 300 nM of the following primers: AP1 (5'-ttttGGTACCaccaaaggatacctgatttg-3'; SEQ ID NO:19) and BP3 (5'-gttaatcagt aacttatgttgcatcacggagatgagagagagag-3'; SEQ ID NO:27). Run the PCR exactly as described in (156).

Step 2b: Use PCR to amplify the GABAlde DeHase gene from 500 ng of DNA from *E. coli* strain K12. Add 300 nM of the following primers: 5'GALD (5'-atgcaacataagttactgattaac-3'; SEQ ID NO:28) and 3'GALD (5'-ttaatgtttaaccatgacgtgg-3'; SEQ ID NO:29). Run the PCR as described in (156).

Step 2c: Use PCR to amplify the NOS terminator with a short overlap for the 3' end of GABAlde DeHase at the 5' end of the NOS terminator using 500 ng of pPV1. Add 300 nM of the following primers BP4 (5'-ccacgtcatggttaaacattaagctac-cgagctcgaatttcc-3'; SEQ ID NO:30) and BP6 (5'-ttttTCTA-GAaacgacggccagtgaattccc-3'; SEQ ID NO:31). Run the PCR as described in (156).

Step 2d: Combine the fragments from Example 3: steps 2a, 2b, and 2c and 300 nM of the following primers BP2 (5'-ttttttttTCTAGAgatatttgagcaaaactgtgg-3'; SEQ ID NO:32) and BP5 (5'-ttttttttCTGCAGgatctagtaacatagatgacac-3'; SEQ ID NO:33). Run the PCR as described in (156). Clone the amplified DNA fragment into pCR4.0-TOPO as described by the manufacturer (Invitrogen).

Step 2e: Transform *E. coli*, select for antibiotic resistance, conduct PCR identification of cloned DNA constructs in transformants, purify the plasmid DNA to confirm its identity and the fidelity of the sequence as described in Example 1: step 1e. Digest the plasmid with XbaI and PstI, isolate the DNA fragment and ligate into the vector pCAMBIA1300 that has been predigested with XbaI and PstI.

Step 3: Ligate the AtGAD1 promoter-PAT-NOS terminator construct upstream of the AtGAD1 promoter-GABAlde DeHase-NOS terminator construct into a plant expression vector.

Step 3a. Digest the pCambia1300-AtGAD1 promoter-PAT-NOS terminator clone (from Example 3: Step 1e) with Acc65I and XbaI, isolate DNA insert and ligate into the vector pCambia1300-AtGAD1 promoter-GABAlde DeHase-NOS terminator (from Example 3: Step 2e) that has been predigested with Acc65I and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 3.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 4.

EXAMPLE 4

Development of a Transgenic Plant that that Non-Constitutively Expresses (AtGAD2 Promoter) PAT and GABAlde DeHase Using Fusion PCR Step 1: Make a DNA construct that contains an AtGAD2 (locus tag At1g65960) promoter with a PAT gene and a NOS terminator in the following manner.

Step 1a: Use PCR to amplify the AtGAD2 promoter (−1714 to −1 bps) with a short overlap for the 5' end of PAT at the 3' end using 500 ng of genomic DNA isolated from an *Arabidopsis thaliana* Col-0. Add 300 nM of the following primers: CP1 (5'-ttttGGTACCtcttac cttgtcctgcaacg-3'; SEQ ID NO:34) and CP3 (5'-cgctcgaaggtaacctgttcatctttgt ttctgtt-tagtgaaag-3'; SEQ ID NO:35). Run the PCR as described in (156).

Step 1b: Use the PAT gene that was amplified in Example 3: Step 1b.

Step 1c: Use the NOS terminator with a short overlap for the 3' end of PAT at the 5' end of the NOS terminator that was amplified in Example 3: Step 1c.

Step 1d: Combine the PCR fragments (Example 4: 1a, 1b, and 1c) and 300 nM of the following primers CP2 (5'-tttttttG-GTACCcgagcttcaacgtagccac-3'; SEQ ID NO:36) and AP5 (5'-tttttttTCTAGAgatctagtaacatagatgacac-3'; SEQ ID NO:26). Run the PCR as described in (156). Clone into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA1300 that has been predigested with Acc65I and XbaI Step 2: Make a DNA construct that contains an AtGAD2 promoter with a GABAlde DeHase gene and a NOS terminator to in the following manner.

Step 2a: Use PCR to amplify the AtGAD2 promoter (−1714 to −1 bps) with a short overlap for the 5' end of GABAlde DeHase at the 3' end of the promoter using 500 ng of genomic DNA isolated from an *Arabidopsis thaliana* Col-0. Add 300 nM of the following primers: CP1 (5'-ttttGGTAC-Ctcttaccttgtcctgcaacg-3'; SEQ ID NO:34) and DP3 (5'-cgctcgaaggt aacctgttcatctttgtttctgtttagtgaaag-3'; SEQ ID NO:37). Run the PCR as described in (156).

Step 2b: Use the GABAlde DeHase gene that was amplified in Example 3: Step 2b.

Step 2c: Use the NOS terminator with a short overlap for the 3' end of GABAlde DeHase at the 5' end of the NOS terminator that was amplified in Example 3: Step 2c.

Step 2d: Combine the PCR fragments (Example 4: 2a, 2b, and 2c) and 300 nM of the following primers DP2 (5'-tttttttC-CATGGcgagcttcaacgtagccac-3'; SEQ ID NO:38) and BP5 (5'-tttttttCTGCAGgatctagtaacatagatgacac-3'; SEQ ID NO:33). Run the PCR as described in (156). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and PstI, isolate the DNA fragment and ligate into the vector pCAMBIA1300 that has been predigested with XbaI and PstI.

Step 3: Ligate the AtGAD2 promoter-PAT-NOS terminator construct upstream of the AtGAD2 promoter-GABAlde DeHase-NOS terminator construct into a plant expression vector.

Step 3a. Digest the pCambia1300-AtGAD2 promoter-PAT-NOS terminator clone (from Example 4: Step 1e) with Acc65I and XbaI, isolate DNA insert and ligate it into the vector pCambia1300-AtGAD2 promoter-GABAlde DeHase-NOS terminator (from Example 4: Step 2e) that has been predigested with Acc65I and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 3.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 4.

EXAMPLE 5

Development of a Transgenic Plant that Constitutively Expresses (AtPHYB promoter) PAT and GABAlde DeHase Using Fusion PCR Step 1: Make a DNA construct that contains an AtPHYB (locus tag At2g18790) promoter with a PAT gene and a NOS terminator in the following manner.

Step 1a: Use PCR to amplify the AtPHYB promoter (−1960 to −1 bps) with a short overlap for the 5' end of PAT at the 3' end using 500 ng of genomic DNA isolated from an *Arabidopsis thaliana* Col-0. Add 300 nM of the following primers: EP 1 (5'-ccaatgcctaataatgtctagc-3'; SEQ ID NO:39) and EP3 (5'-cgctcgaaggtaacctgttcatgccgtttgatttt gaatttgag-3'; SEQ ID NO:40). Run the PCR exactly as described in (156).

Step 1b: Use the PAT gene that was amplified in Example 3: Step 1b.

Step 1c: Use the NOS terminator with a short overlap for the 3' end of PAT at the 5' end of the NOS terminator that was amplified in Example 3: Step 1c.

Step 1d: Combine the PCR fragments (Example 4: 1a, 1b, and 1c) and 300 nM of the following primers EP2 (5'-tttttttG-GTACCattcttgaattacgattgtacc-3'; SEQ ID NO:41) and AP5 (5'-tttttttTCTAGAgatctagtaacatagatgacac-3'; SEQ ID NO:26). Run the PCR as described in (156). Clone into pCR4.0-TOPO as described by the manufacturer (Invitrogen).

Step 1e. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA1300 that has been predigested with Acc65I and XbaI.

Step 2: Make a DNA construct that contains an AtPHYB promoter with a GABAlde DeHase gene and a NOS terminator to in the following manner.

Step 2a: Use PCR to amplify the AtPHYB promoter (−1960 to −1 bps) with a short overlap for the 5' end of GABAlde DeHase at the 3' end using 500 ng of genomic DNA isolated from an *Arabidopsis thaliana* Col-0. Add 300 nM of the following primers: EP1 (5'-ccaatgcctaa taatgtctagc-3'; SEQ ID NO:22) and FP3 (5'-gttaatcagtaacttatgttgcatgc-cgtttgattftgaatttgag-3'; SEQ ID NO:42). Run the PCR as described in (156).

Step 2b: Use the GABAlde DeHase gene that was amplified in Example 3: Step 2b.

Step 2c: Use the NOS terminator with a short overlap for the 3' end of GABAlde DeHase at the 5' end of the NOS terminator that was amplified in Example 3: Step 2c.

Step 2d: Combine the PCR fragments (Example 4: 2a, 2b, and 2c) and 300 nM of the following primers FP2 (5'-tttttttTCTAGAattcttgaattacgattgtacc-3'; SEQ ID NO:43) and BP5 (5'-tttttttCTGCAGgatctagtaacatagatgacac-3'; SEQ ID NO:33). Run the PCR as described in (156). Clone into pCR4.0-TOPO as described by the manufacturer (Invitrogen).

Step 2e: Transform *E. coli*, select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and PstI, isolate DNA fragment and ligate into the vector pCAMBIA1300 that has been predigested with XbaI and PstI.

Step 3: Ligate the AtPHYB promoter-PAT-NOS terminator construct upstream of the AtGAD2 promoter-GABAlde DeHase-NOS terminator construct into a plant expression vector.

Step 3a. Digest the pCambia1300-AtPHYB promoter-PAT-NOS terminator clone (from Example 4: Step 1e) with Acc65I and XbaI, isolate DNA insert and ligate it into the vector pCambia1300-AtGAD2 promoter-GABAlde DeHase-NOS terminator (from Example 4: Step 2e) that has been predigested with Acc65I and XbaI. Transform the DNA construct into *E. coli*, select for antibiotic resistance and confirm the presence of the DNA construct with PCR or by restriction digest analysis.

Step 4: Transform *Agrobacterium tumefaciens*: Transform the DNA construct into *Agrobacterium tumefaciens*, select for antibiotic resistance and confirm the presence of the DNA construct as described in Example 1: Step 3.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 4.

EXAMPLE 6

Development of a Transgenic Plant that Non-Constitutively Expresses (AtGAD1 Promoter) Pat Using Fusion PCR Step 1: Make a DNA construct that contains an AtGAD1 (locus tag At5g17330) promoter with a PAT gene and a NOS terminator in a binary vector such as pCambia 1300 (Example 3: Step 1) in the following manner Step 2: Transform *Agrobacterium tumefaciens*: Transform the DNA construct into *Agrobacterium tumefaciens*, select for antibiotic resistance and confirm the presence of the DNA construct as described in Example 1: Step 3.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 4.

EXAMPLE 7

Development of a Transgenic Plant that Non-Constitutively Expresses (AtGAD1 Promoter) and GABAlde DeHase Using Fusion PCR Step 1: Make a DNA construct that contains an AtGAD1 (locus tag At5g17330) promoter with a GABAlde DeHase gene and a NOS terminator in a binary vector such as pCambia 1300 (Example 3: Step 2).

Step 2: Transform *Agrobacterium tumefaciens*: Transform the DNA construct into *Agrobacterium tumefaciens*, select for antibiotic resistance and confirm the presence of the DNA construct as described in Example 1: Step 3.

Step 5: Transform plant, *Arabidopsis thaliana*: Transform the construct into *Arabidopsis thaliana*, select for antibiotic resistance, select for homozygote plants and confirm the presence of the DNA constructs as described in Example 1: Step 4.

EXAMPLE 8

Development of a Transgenic Plant that Non-Constitutively Expresses (AtGAD1 promoter) PAT in a Plant Using Chemical Synthesis Step 1: Use chemical synthesis to make a DNA construct that contains a tissue-specific promoter, AtGAD1, fused with SEQ ID NO: 1, 44, 45, 46, 47 or 48 and a NOS terminator. Clone the DNA construct into a binary vector, such as pCambia1300, pCambia2300 or pCambia3200. The PAT genes are as follows:

SEQ ID NO:1 encodes a PAT peptide from *Escherichia coli;*

SEQ ID NO 44 encodes a PAT peptide from *Lactobacillus brevis* optimized for expression in canola (*Brassica napus* L.), a dicot;

SEQ ID NO 45 encodes a PAT peptide from *L. brevis* optimized for expression in corn (*Zea mays*), a moncot;

SEQ ID NO 46 encodes a PAT peptide from *Erwinia carotovora* optimized for expression in canola (*Brassica napus* L.), a dicot;

SEQ ID NO 47 encodes a PAT peptide from *Coprothermobacter proteolyticus* optimized for expression *Arabidopsis*, a dicot; and SEQ ID NO 48 encodes a PAT peptide from *Meiothermus ruber* optimized for expression *Arabidopsis*, a dicot.

Step 2: Transform *Agrobacterium tumefaciens*: Transform the DNA construct into *Agrobacterium tumefaciens*, select for antibiotic resistance and confirm the presence of the DNA construct.

Step 3: Transform plant (*Arabidopsis*, soybean, corn, camelina, canola, rice, cotton, wheat, sugar beet, sugarcane, or sorghum), select for transgenic plants. Confirm the presence of the DNA constructs in the transgenic plants.

EXAMPLE 9

Development of a Transgenic Plant that Non-Constitutively Expresses (AtGAD1 Promoter) PAT-GABAlde DeHase in a Plant Using Chemical Synthesis Step 1: Use chemical synthesis to make a DNA construct that contains a tissue-specific promoter, AtGAD1, fused with SEQ ID NO: 1, 44, 45, 46, 47 or 48 and a NOS terminator together with a tissue-specific promoter, AtGAD1, fused with SEQ ID NO: 3, 49 or 50 and a NOS terminator. Clone the DNA construct into a binary vector, such as pCambia1300, pCambia2300 or pCambia3200. The GABAlde DeHase genes are as follows:

SEQ ID NO:3 encodes a GABAlde DeHase peptide from *E. coli;*

SEQ ID NO 49 encodes a GABAlde DeHase peptide from *L. brevis* optimized for expression in *Arabidopsis*, a dicot; and SEQ ID NO 50 encodes a GABAlde DeHase peptide from *E. carotovora* optimized for expression in *Arabidopsis*, a dicot.

Step 2: Transform *Agrobacterium tumefaciens*: Transform the DNA construct into *Agrobacterium tumefaciens*, select for antibiotic resistance and confirm the presence of the DNA construct.

Step 3: Transform plant (*Arabidopsis*, soybean, corn, rice, camelina or canola), select for antibiotic resistance, select for transgenic plants. Confirm the presence of the DNA construct in the transgenic plants.

EXAMPLE 10

Increased GABA Levels in Transgenic Plants with the PAT or PAT-GABAlde DeHase Transgenes PAT was expressed either alone or with GABAlde DeHase in *Arabidopsis* plants using the AtGAD1 promoter Immunoblot analysis as described in (168) was used to determine GABA levels in shoot (leaves) and root samples of 30-day-old plants. Table 1 shows the results of the analysis. In the shoots, GABA levels were 5 to 6.5 times higher in AtGAD1::PAT-GABAlde DeHase and AtGAD2::PAT-GABAlde DeHase compared to WT, respectively. In the roots, GABA levels were twice as high in AtGAD1::PAT and over 4 times higher in AtGAD1::PAT-GABAlde DeHase compared to WT. Thus, for the AtGAD2 line, GABA was higher in the shoots of the transgenic plants compared to WT, and for the AtGAD1 lines, GABA was higher in the roots of the transgenic plants compared to WT.

TABLE 1

GABA levels in the shoots and roots of the transgenic and WT plants in units of ug per gram of wet weight (GWW)

| LINE | Shoot [GABA] (ug/GWW) | Root [GABA] (ug/GWW) |
| --- | --- | --- |
| WT | 2.7 | 3.5 |
| AtGAD1::PAT | 3.8 | 7.6 |
| AtGAD1::PAT-GABAlde DeHase | 13.7 | 17.1 |
| AtGAD2::PAT-GABAlde DeHase | 17.6 | 3.8 |

EXAMPLE 11

Effects of the PAT and PAT-GABAlde DeHase Transgenes on Plant Growth

11A. Transgenic dicot plants with the PAT or PAT-GABAlde DeHase gene construct are larger than WT plants PAT was expressed either alone or with GABAlde DeHase in *Arabidopsis* plants using the AtGAD1 promoter. Plants were maintained under standard growth conditions (20-21° C., under cool white fluorescent lights (120 umol of photons per m$^2$ per s) with a 16-h light/8-h dark cycle) in soil (PREMIER ProMix BX). Plant size was measured on 28-day-old transgenic and WT plants. Plant height and average leaf area were determined on 20 plants from each line. Plant height measurements were taken from the base of the plant to the top of plant stalk. For leaf area, a representative plant from each transgenic line was imaged using a digital camera, and four representative leaves from each plant were digitized. Mean plant height and leaf area were determined for each line and are listed in Table 2. At day 28, the transgenic plants, on average, were more than twice the height of the WT plants and had leaf areas that were 50% to 100% larger than the WT plants.

TABLE 2

Mean plant height and leaf area for 28-day old transgenic and WT lines

| LINE | HEIGHT (cm) Mean (SD) | LEAF AREA (cm$^2$) Mean (SD) |
| --- | --- | --- |
| WT | 2.17 (1.62) | 2.92 (0.18) |
| AtGAD1::PAT | 4.88 (2.49) | 4.56 (0.58) |
| AtGAD1::PAT:-GABAlde DeHase | 5.21 (3.18) | 6.22 (0.56) |

Figure 2:
FIG. 2 shows representative 26-day-old plants grown in limited N media. AtGAD2::PAT-GABAlde DeHase (two left-most plants), WT (two center plants), and AtGAD1::PAT-GABAlde DeHase (two right-most plants).

11B. Transgenic dicot plants with the PAT-GABAlde DeHase gene construct have larger roots than WT when grown in limited nitrogen media PAT was expressed with GABAlde DeHase in *Arabidopsis* plant using either the AtGAD1 or AtGAD2 promoter. Shown in FIG. 2 are 26-day-old plants that were grown in nitrogen-limited media (MS with 1/60 of normal [Nitrogen]). The two left plants are AtGAD2::PAT-GABAlde DeHase, the two center plants are WT, and the two right plants are AtGAD1::PAT-GABAlde DeHase. Compared to WT the transgenic plants had bigger and greener leaves and more developed root systems, which indicate a better uptake system for nutrients and water.

11C. Transgenic dicot plants with the PAT or PAT-GABAlde DeHase gene constructs have greater yield than WT when grown in limited or sufficient nitrogen media To demonstrate that the transgenic plants expressing PAT and/or PAT-GABAlde DeHase have increased yield compared to WT plants when grown under limited or sufficient nitrogen conditions, the yield of three transgenic lines, AtGAD1::PAT, AtGAD1::PAT-GABAlde DeHase, and AtGAD2::PAT-GABAlde DeHase, was compared to that of WT *Arabidopsis* plants. Eight plants for each of the four lines were grown in vermiculite::soil (PREMIER ProMix BX) mix (2::1, V::S) supplemented with nitrate added back in at either 0 (limited-nitrogen condition) or 1 mM (sufficient-nitrogen condition). The plants were grown under standard growth conditions until day 45 when watering and nitrogen addition stopped. Seeds were collected, cleaned, and weighed when the plants were dry. Table 3 shows the yield data. The average total seed weight per plant was higher in all the transgenic lines relative to WT for both limited and sufficient nitrogen conditions.

TABLE 3

Yield (mg, total seed per plant) of transgenic and WT plants grown in limited or sufficient nitrogen conditions

| LINE | LIMITED N Mean (SD) | SUFFICIENT N Mean (SD) |
| --- | --- | --- |
| WT | 9.8 (3.9) | 42.9 (7.4) |
| AtGAD1::PAT | 12.2 (5.9) | 52.2 (7.0) |
| AtGAD1::PAT-GABAlde DeHase | 10.9 (2.9) | 47.4 (5.1) |
| AtGAD2::PAT-GABAlde DeHase | 14.3 (3.6) | 59.6 (15.5) |

11D. Transgenic plants with distinct PAT gene constructs have different increases in yield To demonstrate that the transgenic plants expressing distinct PAT genes have different increases in yield, transgenic *Arabidopsis* plants were independently transformed with AtGAD1 promoter with SEQ ID NO: 1 (AtGAD1::PAT1), AtGAD1 promoter with SEQ ID NO: 45 (AtGAD1::PAT2), and EVC. For each of the constructs, eight independent lines were grown in limited nitrogen media for 60 days under standard growth conditions. After the plants dried the seeds were harvested and weighed. The total seed weight in AtGAD 1::PAT1 and AtGAD 1::PAT2 were 13.3% and 22% greater than the ECV lines.

Figure 3:
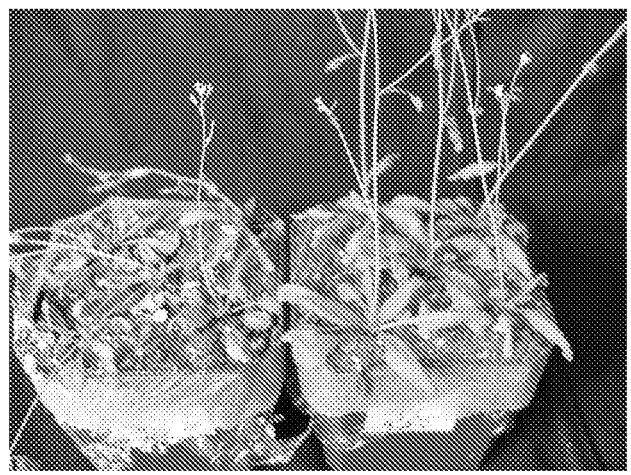
FIG. 3 shows representative 41-day-old plants after 20 days of drought: WT (left) and AtGAD1::PAT (right).

11E. Transgenic dicot plants with the PAT or PAT-GABAlde DeHase gene constructs have greater yield than WT when subjected to drought To demonstrate that the transgenic plants expressing PAT and/or PAT-GABAlde DeHase have increased yield compared to WT plants when subjected to drought, the yield of two transgenic lines, AtGAD1::PAT and AtGAD1::PAT-GABAlde DeHase, was compared to that of WT *Arabidopsis* plants. Plants were grown and maintained under standard growth conditions (three pots per line and five plants per pot) in a soil peat mix (PREMIER ProMix BX). The surface of each pot was covered with plastic to minimize the loss of water through soil evaporation. The plants were watered by sub-irrigation for 21 days and then left to dry. When dried the seeds were collected and yield was determined. For each of three pots, the mean seed yield per plant was determined by weighing the total seed yield per pot and dividing by 5. The average yield per plant per line was determined by calculating the mean of the three means. The means (standard error of the means) for the WT, AtGAD1::PAT and AtGAD1::PAT-GABAlde DeHase lines are 8.7 (2.5), 12.7 (3.1), and 10.5 (3.2) mg/plant, respectively. Thus, when subjected to drought the average yields of the AtGAD1::PAT and AtGAD1::PAT-GABAlde DeHase transgenic plants are 56% and 46% greater than that of the WT plants. FIG. 3 shows a representative 41-day-old WT plant (left) and a AtGAD1::PAT plant (right) after 20 days of drought. The transgenic plants showed less wilting than WT.

11F. Transgenic dicot plants with the PAT or PAT-GABAlde DeHase gene constructs have greater survival rates compared to WT plants when subjected to high temperature To determine if insertion of the PAT or PAT-GABAlde DeHase genes conveyed tolerance to heat we used a thermal tolerance assay described in (169). *Arabidopsis* seedlings (36 seeds/plate×3 replicates per exposure duration) were plated on MS plus vitamins 1.1% phytablend and maintained under standard growth conditions. On day 7, the seedlings were exposed to 38° C. for 90 min (pre-treatment) followed by 22° C. for 120 min then 45° C. for 120 min. The plates were then returned to 22° C. Percent survival was determined one week later. The WT line had a 24% survival rate whereas the transgenic lines, AtGAD1::PAT and AtGAD1::PAT-GABAlde DeHase, had survival rates of 97% and 79%, respectively.

11G. Transgenic monocot plants with the PAT or PAT-GABAlde DeHase gene constructs have greater dry root weight compared to WT plants in limited and sufficient nutrient media In corn, dry root weight is highly correlated to yield (170). We used this information to devise a novel short-term assay to test corn plants for increased NUE under N-limited conditions. Expression of the PAT and PAT-GABAlde DeHase genes were under the control of the rolC promoter (171). For each line, 24 siblings (12 transgenic and 12 null-controls were tested in N-limited conditions. The null-control plants are siblings of the transgenic plants that do not contain the transgenes. The transgenic and null plants were grown in six-inch circular plastic pots. For the limited nutrient conditions the pots were filled with 600 g of 3 parts vermiculite and 1 part soil (Metro-Mix 360, Sun Gro Horticulture, USA). For the sufficient nutrient conditions the pots were filled with 600 g of a soil/peat mix (Metro-Mix 360, Sun Gro Horticulture, USA). The plants were maintained under standard conditions except the light level was 450 umol of photons per m$^2$ per s. The plants were watered as necessary by subirrigation. At day 39 the roots of the plants were harvested and dried for 10 days prior to being weighed. The dry root weight of the transgenic plants was compared with that of the null-control plants. The sample size for the rolC::PAT-GABAlde DeHase construct was 40 plants from 3 independent lines. The sample size for the rolC::PAT construct was 104 plants from 7 independent lines. The results of the bioassay show that the dry root weight of the transgenic plants with PAT-GABAlde DeHase were on average, 22% and 31% greater than the null-control plants in limited and sufficient nutrient conditions, respectively. The average nitrogen, phosphorus and potassium content in the limited nutrient condition for the PAT-GABAlde DeHase construct were 20.1, 2.4 and 50 ppm, respectively. In the sufficient-nutrient condition, the average nitrogen, phosphorus, and potassium content for PAT-GABAlde DeHase construct were 65.7, 4.6, and 157 ppm, respectively. In the limited-nutrient condition, the dry root weight of the transgenic plants with the PAT transgene was, on average, 12% greater than the null-control plants. The average nitrogen, phosphorus, and potassium content for the PAT construct were 3.2, 0.43 and 48.9 ppm.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Bown et al., 1997. "The metabolism and functions of [gamma]-aminobutyric acid." Plant Physiol, 115: 1-5.

2. Breitkreuz et al., 1999. "Identification and characterization of GABA, proline and quaternary ammonium compound transporters from *Arabidopsis thaliana*." FEBS Lett, 450: 280-4.
3. Snedden et al., 1999. Regulation of the g-aminobutyrate-synthesizing enzyme, glutamate decarboxylase, by calcium/cadmodulin: a mechanism for rapid activation in response to stress. In: Lerner H, editor. Plant Responses to Environmental Stresses: From Phytohormones to Genome Reorganization 549-574. New York: Marcel Dekker Inc.
4. Kinnersley et al., 2000. "Receptor modifiers indicate that GABA is a potential modulator of ion transport in plants." Plant Growth Reg, 9: 137-146.
5. Bouché et al., 2003. "Mitochondrial succinic-semialdehyde dehydrogenase of the gamma-aminobutyrate shunt is required to restrict levels of reactive oxygen intermediates in plants." Proc Natl Acad Sci USA, 100: 6843-8.
6. Bouche et al., 2004. "The root-specific glutamate decarboxylase (GAD1) is essential for sustaining GABA levels in *Arabidopsis*." Plant Mol Biol, 55: 315-25.
7. Streeter et al., 1972. "In vivo and in vitro studies on g-aminobutyric acid metabolism with the radish plant (*Raphanus sativus*)." Plant Physiology, 49: 572-584.
8. Davies 1980. Anaerobic metabolism and the production of organic acids. In: Davies D D, editor. The Biochemistry of Plants 581-611. New York: Academic Press.
9. Selman et al., 1978. "Changes in the free amino compounds in young tomato plants in light and darkness with particular reference to g-aminobutyric acid." Ann Bot, 42: 627-636.
10. Wallace et al., 1984. "Rapid accumulation of g-aminobutyric acid and alanine in soybean leaves in response to an abrupt transfer to lower temperature, darkness or mechanical manipulation." Plant Physiology, 75: 170-175.
11. Ramputh et al., 1996. "Rapid g-aminobutyric acid synthesis and the inhibition of the growth and development of oblique-banded leaf-roller larvae." Plant Physiology, 111: 1349-1354.
12. MacGregor et al., 2003. "Overexpression of glutamate decarboxylase in transgenic tobacco plants deters feeding by phytophagous insect larvae." J Chem Ecol, 29: 2177-82.
13. Palanivelu et al., 2003. "Pollen tube growth and guidance is regulated by POP2, an *Arabidopsis* gene that controls GABA levels." Cell, 114: 47-59.
14. Beuve et al., 2004. "Putative role of g-aminobutyric acid (GABA) as a long-distance signal in up-regulation of nitrate uptake in *Brassica napus* L." Plant Cell Environ,
15. Baum et al., 1996. "Calmodulin binding to glutamate decarboxylase is required for regulation of glutamate and GABA metabolism and normal development in plants." Embo J, 15: 2988-96.
16. Arazi et al., 1995. "Molecular and biochemical analysis of calmodulin interactions with the calmodulin-binding domain of plant glutamate decarboxylase." Plant Physiology, 108: 551-561.
17. Turano et al., 1998. "Characterization of two glutamate decarboxylase cDNA clones from *Arabidopsis thaliana*." Plant Physiol, 117: 1411-1421.
18. Fromm et al., 1998. Role of Ca2+/calmodulin in plant response to abiotic stress: a review. In: Altman A and Zik M, editors. Hort. Biotech In Vitro Cult and Breeding 431-438: Acta Hort.
19. Breitreuz et al., 1995. "Subcellular compartmentation of the 4-aminobutyrate shunt in protoplasts from developing soybean cotyledons." Plant Physiology, 108: 99-103.
20. Flores et al., 1985. "Polyamine catabolism in higher plants: characterization of pyrroline dehydrogenase." Plant Growth Regul, 3: 277-291.
21. Matsuda et al., 1984. "gamma-Guanidinobutyraldehyde dehydrogenase of *Vicia faba* leaves." Plant Physiol, 76: 654-657.
22. Shelp et al., 1999. "Metabolism and functions of gamma-aminobutyric acid." Trends in Plant Sci, 41: 446-452.
23. Snedden et al., 1995. "Calcium/Calmodulin activation of soybean glutamate decarboxylase." Plant Physiology, 108: 543-549.
24. Zik et al., 1998. "Two isoforms of glutamate decarboxylase in *Arabidopsis* are regulated by calcium/calmodulin and differ in organ distribution." Plant Mol Biol, 37: 967-975.
25. Kinnersley et al., 2000. "Gamma-aminobutyric acid (GABA) and plant responses to stress." Crit. Rev Plant Sci, 19: 479-509.
26. Baum et al., 1993. "A plant glutamate decarboxylase containing a calmodulin binding domain. Cloning, sequence, and functional analysis." Journal of Biological Chemistry, 268: 19610-19617.
27. Van Cauwenberghe et al., 2002. "Plant pyruvate-dependent gamma-aminobutyrate transaminase: identification of an *Arabidopsis* cDNA and its expression in *Escherichia coli*." Canadian Journal of Botany, 80: 933-941.
28. Busch et al., 1999. "Plant succinic semialdehyde dehydrogenase. Cloning, purification, localization in mitochondria, and regulation by adenine nucleotides." Plant Physiol, 121: 589-97.
29. Busch et al., 2000. "Plant succinic semialdehyde dehydrogenase: dissection of nucleotide binding by surface plasmon resonance and fluorescence spectroscopy." Biochemistry, 39: 10110-7.
30. Breitkreuz et al., 2003. "A novel gamma-hydroxybutyrate dehydrogenase: identification and expression of an *Arabidopsis* cDNA and potential role under oxygen deficiency." J Biol Chem, 278: 41552-6.
31. Shaibe et al., 1985. "Control of utilization of L-arginine, L-ornithine, agmatine, and putrescine as nitrogen sources in *Escherichia coli* K-12." J Bacteriol, 163: 938-42.
32. Shaibe et al., 1985. "Metabolic pathway for the utilization of L-arginine, L-ornithine, agmatine, and putrescine as nitrogen sources in *Escherichia coli* K-12." J Bacteriol, 163: 933-7.
33. Samsonova et al., 2003. "Molecular cloning and characterization of *Escherichia coli* K12 ygjG gene." BMC Microbiol, 3:2.
34. Samsonova et al., 2005. "Identification of *Escherichia coli* K12 YdcW protein as a gamma-aminobutyricaldehyde dehydrogenase." FEBS Left, 579: 4107-12.
35. Kinnersley 1995. U.S. Pat. No. 5,439,873.
36. Kinnersley et al., 1997. U.S. Pat. No. 5,604,177.
37. Kinnersley et al., 2003. U.S. Pat. No. 2,003,0046732.
38. Shelp et al., 2003. U.S. Pat. No. 2,003,0110530.
39. Palaivelu et al., 2004. U.S. Pat. No. 2,004,0177398.
40. Breitkreuz et al., 2000. Canada Patent No. 02368953.
41. Murray et al., 1989. "Codon usage in plant genes." Nucleic Acids Res., 17: 477-498.
42. Langenheim et al., 1982. Botany: Plant biology and its relation to human affairs. John Wiley & Sons Inc.: New York.
43. Vasil 1984. Cell culture and somatic cell genetics of plants, Laboratory procedures and their applications ( ). Orlando: Academic Press.
44. Stanier et al., 1986. The microbial world, 5th ed., New Jersey: Prentice-Hall.
45. Dhringra et al., 1985. Basic plant pathology methods. Boca Raton, Fla.: CRC Press.

46. Maniatis et al., 1985. Molecular Cloning: A Laboratory Manual; DNA Cloning. New York: Cold Spring Harbor.
47. Gait 1984. Oligonucleotide Synthesis—A Practical Approach. Washington, D.C.: IRL Press.
48. Hames et al., 1984. Nucleic acid hybridization, a practical approach. Washington D.C.: IRL Press.
49. Watson et al., 1992. Recombinant DNA. New York: Scientific American Books.
50. van Der Krol et al., 1999. "Developmental and wound-, cold-, desiccation-, ultraviolet-B-stress-induced modulations in the expression of the petunia zinc finger transcription factor gene ZPT2-2." Plant Physiol, 121: 1153-62.
51. Shinmyo et al., 1998. "Metabolic engineering of cultured tobacco cells." Biotechnol Bioeng, 58: 329-32.
52. Sohal et al., 1999. "The promoter of a *Brassica napus* lipid transfer protein gene is active in a range of tissues and stimulated by light and viral infection in transgenic *Arabidopsis*." Plant Mol Biol, 41: 75-87.
53. Eulgem et al., 1999. "Early nuclear events in plant defence signalling: rapid gene activation by WRKY transcription factors." Embo J, 18: 4689-99.
54. Cormack et al., 2002. "Leucine zipper-containing WRKY proteins widen the spectrum of immediate early elicitor-induced WRKY transcription factors in parsley." Biochim Biophys Acta, 1576: 92-100.
55. Lebel et al., 1998. "Functional analysis of regulatory sequences controlling PR-1 gene expression in *Arabidopsis*." Plant J, 16: 223-33.
56. Ngai et al., 1997. "Light-induced transcriptional repression of the pea AS1 gene: identification of cis-elements and transfactors." Plant J, 12: 1021-34.
57. Kucho et al., 1999. "CO (2)-responsive transcriptional regulation of CAH1 encoding carbonic anhydrase is mediated by enhancer and silencer regions in *Chlamydomonas reinhardtii*." Plant Physiol, 121: 1329-38.
58. Kucho et al., 2003. "Cis-acting elements and DNA-binding proteins involved in CO2-responsive transcriptional activation of Cah1 encoding a periplasmic carbonic anhydrase in *Chlamydomonas reinhardtii*." Plant Physiol, 133: 783-93.
59. Chen et al., 1999. "The auxin, hydrogen peroxide and salicylic acid induced expression of the *Arabidopsis* GST6 promoter is mediated in part by an ocs element." Plant J, 19: 667-77.
60. Chen et al., 1996. "The promoter of a H2O2-inducible, *Arabidopsis* glutathione S-transferase gene contains closely linked OBF- and OBP1-binding sites." Plant J, 10: 955-66.
61. Lu et al., 1998. "Sugar response sequence in the promoter of a rice alpha-amylase gene serves as a transcriptional enhancer." J Biol Chem, 273: 10120-31.
62. Leubner-Metzger et al., 1998. "Ethylene-responsive element binding protein (EREBP) expression and the transcriptional regulation of class I beta-1,3-glucanase during tobacco seed germination." Plant Mol Biol, 38: 785-95.
63. Hudspeth et al., 1992. "Expression of Maize Phosphoenolpyruvate Carboxylase in Transgenic Tobacco: Effects on Biochemistry and Physiology." Plant Physiol, 98: 458-464.
64. de Framond 1991. "A metallothionein-like gene from maize (*Zea mays*). Cloning and characterization." FEBS Lett, 290: 103-6.
65. Hudspeth et al., 1996. "Characterization and expression of metallothionein-like genes in cotton." Plant Mol Biol, 31: 701-5.
66. Herrera-Estrella et al., 1983. "Expression of chimaeric genes transferred into plant cells using a Ti-plasmid-derived vector." Nature, 303: 209-213.
67. Pathirana et al., 1997. "Analyses of phosphoenolpyruvate carboxylase gene structure and expression in alfalfa nodules." Plant J, 12: 293-304.
68. Yang et al., 2002. "Isolation and characterization of the orchid cytokinin oxidase DSCKX1 promoter." J. Exper, Bot., 53: 1899-1907.
69. Moon et al., 2004. "Developmental regulation of peach ACC oxidase promoter-GUS fusions in transgenic tomato fruits." J Exper Bot, 55: 1519-1528.
70. Avsian-Kretchmer et al., 2004. "The salt-stress signal transduction pathway that activates the gpx1 promoter is mediated by intracellular H2O2, different from the pathway induced by extracellular H2O2." Plant Physiol, 135: 1685-96.
71. Wu et al., 2007. "Functional analysis of a cotton glucuronosyltransferase promoter in transgenic tobaccos." Cell Research 17: 174-183.
72. Gallego et al., 1995. "A role for glutamate decarboxylase during tomato ripening: the characterisation of a cDNA encoding a putative glutamate decarboxylase with a calmodulin-binding site." Plant Mol Biol, 27: 1143-1151.
73. Yun et al., 1998. "Cloning and characterization of tobacco cDNA encoding calcium/calmodulin-dependent glutamate decarboxylase." Mol Cells: 125-129.
74. Oh et al., 2005. "Cloning and characterization of a rice cDNA encoding glutamate decarboxylase." J. Biochem. Mol. Biol., 38: 595-601.
75. An et al., 1985. "New cloning vehicles for transformation of higher plants." EMBO. J., 4: 277-284.
76. Gruber et al., 1993. Vectors for plant transformation. In: Glick B R and Thompson J E, editors. Methods in Plant Molecular Biology and Biotechnology 89-119. Baco Raton, Fla.: CRC Press.
77. Ausubel et al., 1995. Current protocols in molecular biology. New York: Greene Publishing and Wiley-Interscience.
78. Ohme-Takagi et al., 1993. "The effect of sequences with high AU content on mRNA stability in tobacco." Proc Natl Acad Sci USA, 90: 11811-5.
79. Newman et al., 1993. "DST sequences, highly conserved among plant SAUR genes, target reporter transcripts for rapid decay in tobacco." Plant Cell, 5: 701-14.
80. von Heijne 1986. "Mitochondrial targeting sequences may form amphiphilic helices." EMBO J, 5: 1335-1342.
81. Swinkels et al., 1991. "A novel, cleavable peroxisomal targeting signal at the amino-terminus of the rat 3-ketoacyl-CoA thiolase." Embo J, 10: 3255-62.
82. Rusch et al., 1995. "Protein transport via amino-terminal targeting sequences: common themes in diverse systems." Mol Membr Biol, 12: 295-307.
83. Soll et al., 1998. "Protein translocation into and across the chloroplastic envelope membranes." Plant Mol Biol, 38: 191-207.
84. Gould et al., 1988. "Identification of peroxisomal targeting signals located at the carboxy terminus of four peroxisomal proteins." J Cell Biol, 107: 897-905.
85. Gould et al., 1989. "A conserved tripeptide sorts proteins to peroxisomes." J Cell Biol, 108: 1657-64.
86. McCammon et al., 1994. "An internal region of the peroxisomal membrane protein PMP47 is essential for sorting to peroxisomes." J Cell Biol, 124: 915-25.
87. Cokol et al., 2000. "Finding nuclear localization signals." EMBO Rep, 1: 411-5.
88. Helenius et al., 2001. "Intracellular functions of N-linked glycans." Science, 291: 2364-9.

89. Emanuelsson et al., 2007. "Locating proteins in the cell using TargetP, SignalP and related tools." Nat Protoc, 2: 953-71.

90. Emanuelsson et al., 2000. "Predicting subcellular localization of proteins based on their N-terminal amino acid sequence." J Mol Biol, 300: 1005-16.

91. Bannai et al., 2002. "Extensive feature detection of N-terminal protein sorting signals." Bioinformatics, 18: 298-305.

92. Bendtsen et al., 2004. "Improved prediction of signal peptides: SignalP 3.0." J Mol Biol, 340: 783-95.

93. Hiller et al., 2004. "PrediSi: prediction of signal peptides and their cleavage positions." Nucleic Acids Res, 32: W375-9.

94. Bhasin et al., 2004. "ESLpred: SVM-based method for subcellular localization of eukaryotic proteins using dipeptide composition and PSI-BLAST." Nucleic Acids Res, 32: W414-9.

95. Garg et al., 2005. "Support vector machine-based method for subcellular localization of human proteins using amino acid compositions, their order, and similarity search." J Biol Chem, 280: 14427-32.

96. Bhasin et al., 2005. "PSLpred: prediction of subcellular localization of bacterial proteins." Bioinformatics, 21: 2522-4.

97. Hoglund et al., 2006. "MultiLoc: prediction of protein subcellular localization using N-terminal targeting sequences, sequence motifs and amino acid composition." Bioinformatics, 22: 1158-65.

98. Shatkay et al., 2007. "SherLoc: high-accuracy prediction of protein subcellular localization by integrating text and protein sequence data." Bioinformatics, 23: 1410-7.

99. Emanuelsson et al., 1999. "ChloroP, a neural network-based method for predicting chloroplast transit peptides and their cleavage sites." Protein Sci, 8: 978-84.

100. Claros et al., 1996. "Computational method to predict mitochondrially imported proteins and their targeting sequences." Eur J Biochem, 241: 779-86.

101. Small et al., 2004. "Predotar: A tool for rapidly screening proteomes for N-terminal targeting sequences." Proteomics, 4: 1581-90.

102. Kelley et al., 2000. "Enhanced genome annotation using structural profiles in the program 3D-PSSM." J Mol Biol, 299: 499-520.

103. Shahin 1985. "Totipotency of tomato protoplasts." Theor. Appl. Genet, 69: 235-240.

104. Fromm et al., 1985. "Expression of genes transferred into monocot and dicot plant cells by electroporation." Proc Nat Aca Sci, 82: 5824-5828.

105. Fromm et al., 1986. "Stable transformation of maize after gene transfer by electroporation." Nature, 319: 791-3.

106. Riggs et al., 1986. "Stable transformation of tobacco by electroporation: evidence for plasmid concatenation." Proc Natl Acad Sci USA, 83: 5602-6.

107. D'Halluin et al., 1992. "Transgenic. maize plants by tissue electroporation." Plant Cell 4: 1495-1505, 4: 1495-1505.

108. Laursen et al., 1994. "Production of fertile transgenic maize by electroporation of suspension culture cells." Plant Mol. Biol., 24: 51-61

109. Crossway et al., 1986. "Integration of foreign DNA following microinjection of tobacco mesophyll protoplasts." Mol. Gen. Genet., 202: 179-185.

110. Griesbach 1983. "Protoplast microinjection." Plant Mol. Biol. Rep., q: 32-37.

111. Sporlein et al., 1991. "Lipofectin: direct gene transfer to higher plants using cationic liposomes." Theor. Appl. Genet., 83: 1-5.

112. Ohgawara et al., 1983. "Uptake of liposome-encapsulated plasmid DNA by plant protoplasts and molecular fate of foreign DNA." Protoplasma, 116: 145-148.

113. Deshayes et al., 1985. "Liposome-mediated transformation of tobacco mesophyll protoplasts by an *Escherichia coli* plasmid." Embo J, 4: 2731-7.

114. Christou et al., 1987. "Stable transformation of soybean by electroporation and root formation from transformed callus." Proc Natl Acad Sci USA, 84: 3962-3966.

115. Horsch et al., 1985. "A Simple and General Method for Transferring Genes into Plants Science 227: 1229-1231 (1985))."

116. Paszkowski et al., 1984. "Direct gene transfer to plants." Embo J, 3: 2717-2722.

117. Hooykaas-Van Slogteren et al., 1992. "Expression of Ti plasmid genes in monocotyledonous plants infected with *Agrobacterium tumefaciens*. 1984." Biotechnology, 24: 382-3.

118. Rogers 1986. "Gene transfer in plants: Production of transformed plants using Ti-plasmid vectors." Meth. Enzymol., 118: 627-640.

119. Bevan et al., 1982. "T-DNA of the *Agrobacterium* Ti and Ri plasmids." Ann. Rev. Genet., 16: 357-384.

120. Klein et al., 1988. "Transfer of foreign genes into intact maize cells with high-velocity microprojectiles." Proc Natl Acad Sci USA, 85: 4305-4309.

121. Klein et al., 1988. "Factors influencing gene delivery into *Zea mays* cells by high-velocity microprojectiles." Biotechnology, 6: 559-563

122. McCabe et al., 1988. "Stable transformation of soybean (*Glycine max*) by particle acceleration." Biotechnology, 6: 923-926.

123. Sanford et al., 1993. Optimizing the biolistic process for different biological application. In: In: Wu R (ed), editor. The Methods in Enzymology 483-509. Orlando: Academic Press.

124. Freeman et al., 1984. "A Comparison of Methods for Plasmid Delivery into Plant Protoplasts." Plant and Cell Physiol, 25: 1353-1365.

125. Frame et al., 1994. "Production of fertile transgenic maize plants by silicon carbide whisker-mediated transformation." Plant J., 6.

126. Thompson et al., 1995. "Maize transformation utilizing silicon carbide whiskers: a review." Euphytica, 85: 75-80.

127. Guo et al., 1995. "Laser-mediated gene transfer in rice." Physiol. Plant., 93: 19-24.

128. Badr et al., 2005. "Production of fertile transgenic wheat plants by laser micropuncture." Photochem. Photobiol. Sci., 4: 803-807.

129. Bao et al., 1997. "Transfection of a reporter plasmid into cultured cells by sonoporation in vitro." Ultrasound in Medicine and Biology, 23: 953-959.

130. Finer et al., 2000. "Use of *Agrobacterium* expressing green fluorescent protein to evaluate colonization of sonication-assisted *Agrobacterium*-mediated transformation-treated soybean cotyledons." Lett Appl Microbiol, 30: 406-10.

131. Amoah et al., 2001. "Factors influencing *Agrobacterium*-mediated transient expression of uidA in wheat inflorescence tissue." J Exp Bot, 52: 1135-42.

132. Krens et al., 1982. "In Vitro transformation of plant protoplasts with Ti-plasmid DNA." Nature, 296: 72-74.

133. Bechtold et al., 1998. "In planta *Agrobacterium*-mediated transformation of adult *Arabidopsis thaliana* plants by vacuum infiltration." Methods Mol Biol, 82: 259-66.
134. Kirk et al., 1993. Concise Encyclopedia of Chemical Technology: John Wiley & Sons.
135. Mosbach et al., 1983. "Formation of proinsulin by immobilized *Bacillus subtilis*." Nature, 302: 543-545.
136. Chan et al., 1974. "Structural uniqueness of lactose operator." Nature, 252: 205-209.
137. Goeddel et al., 1980. "Synthesis of human fibroblast interferon by *E. coli*." Nucleic Acids Res, 8: 4057-4074.
138. Sherman et al., 1982. Methods in Yeast Genetics. New York: Cold Spring Harbor Laboratory.
139. Sherman 1991. Getting started with yeast. In: Guthrie C and Fink G R, editors. Methods in Enzymology, Guide to Yeast Genetics and Molecular Biology 3-21. New York: Acad. Press.
140. Meinkoth J et al., 1984. "Hybridization of nucleic acids immobilized on solid supports. Anal Biochem 1984; 138: 267-84." Anal Biochem, 138: 267-284.
141. Tijssen 1993. Overview of principles of hybridization and the strategy of nucleic acid probe assays. Laboratory Techniques in Biochemistry and Molecular Biology—Hybridization with Nucleic Acid Probes, part I: Elsevier, N.Y.
142. Smith et al., 1981. "Comparison of biosequences." Adv. Appl. Math, 2: 482-489.
143. Needleman et al., 1970. "A general method applicable to the search for similarities in the amino acid sequence of two proteins." J. Mol. Biol., 48: 443-453.
144. Pearson et al., 1988. "Improved tools for biological sequence comparison." Proc Natl Acad Sci USA, 85: 2444-2448.
145. Higgins et al., 1989. "Fast and sensitive multiple sequence alignments on a microcomputer." Comput Appl Biosci, 5: 151-3.
146. Higgins et al., 1988. "CLUSTAL: a package for performing multiple sequence alignment on a microcomputer." Gene, 73: 237-44.
147. Higgins et al., 1992. "CLUSTAL V: improved software for multiple sequence alignment." Comput Appl Biosci, 8: 189-91.
148. Feng et al., 1987. "Progressive sequence alignment as a prerequisite to correct phylogenetic trees." J Mol Evol, 25: 351-60.
149. Henikoff et al., 1989. "Amino acid substitution matrices from protein blocks." Proc. Natl. Acad. Sci. USA, 89: 10915-10919.
150. Altschul et al., 1997. "Gapped BLAST and PSI-BLAST: a new generation of protein database search programs." Nucleic Acids Res, 25: 3389-3402.
151. Wootton et al., 1993. "Statistics of local complexity in amino acid sequences and sequence databases." Comput. Chem., 17: 149-163.
152. Wootton et al., 1996. "Analysis of compositionally biased regions in sequence databases." Methods Enzymol, 266: 554-71.
153. Claverie et al., 1993. "Information enhancement methods for large scale sequence analysis." Comput. Chem. 17: 191-201.
154. Myers et al., 1988. "Optimal alignments in linear-space." Computer Applic. Biol. Sci., 4: 11-17.
155. Broothaerts et al. (2005). "Gene transfer to plants by diverse species of bacteria." Nature 433: 629-633.
156. Szewczyk et al. 2006. "Fusion PCR and gene targeting in *Aspergillus nidulans*." Nature Protocols 1:3111-3120.
157. Ho et al. 1989. "Site-directed mutagenesis by overlap extension using the polymerase chain reaction." Gene 77:51-59.
158. Kathiresan et al., 1998. "γ-aminobutyric acid promotes stem elongation in *Stellaria longipes*: the role of ethylene." Plant Growth Reg, 26: 131-137.
159. Guo et al., 2009. "Differentially expressed genes between drought-tolerant and drought-sensitive barley genotypes in response to drought stress during the reproductive stage." J Exp Bot, 60: 3531-3544.
160. Bolarin et al., 1995. "Short-term solute changes in leaves and roots of cultivated and wild tomato seedlings under salinity." *J. Plant Physiol,* 147: 463-468.
161. Aurisano et al., 1995. "Anaerobic accumulation of 4-aminobutyrate in rice seedlings: causes and significance." Phytochemistry, 38: 1147-1150.
162. Wahid et al., 2007. "Heat tolerance in plants: An overview." Environ Exper Bot, 61: 199-223.
163. Jaffe et al., 1979. "Thigmomorphogenesis, the effect of mechanical perturbation on the growth of plants, with special reference to anatomical changes, the role of ethylene and interaction with other environmental stresses." In: Mussell H and Staples R C, editors. Stress Physiology in Crop Plants 25-69. New York: John Wiley & Sons.
164. Allan et al., 2006. "Fluctuations of (γ-aminobutyrate, (γ-hydroxybutyrate and related amino acids in *Arabidopsis* leaves as a function of the light-dark cycle, leaf age and N stress." Can. J. Bot, 84: 1339-1346.
165. Bown et al., 2006. "Gamma-aminobutyrate: defense against invertebrate pests?" Trends Plant Sci, 11: 424-427.
166. Narayan et al., 1990. "Metabolism, enzymology and possible roles of 4-amino butyrate in higher plants." Phytochem, 29: 367-375.
167. Roberts, 2007. "Does GABA Act as a Signal in Plants? Hints from Molecular Studies." Plant Signaling & Behavior, 2: 408-409.
168. Palanivelu et al., 2002. U.S. Pat. No. 7,109,149.
169. Hong et al., 2000. "Mutants of *Arabidopsis thaliana* defective in the acquisition of tolerance to high temperature stress." PNAS USA, 97: 4392-7.
170. Rad, et al., 2010. "Assessing difference soil water contents on corn root development." World Applied Sciences Journal, 8: 694-9.
171. Schmidling et al., 1989. "Promoters of the rolA, B, and C genes of *Agrobacterium rhizogenes* are differentially regulated in tramgenic plants." Plant Cell 1: 665-670.

What is claimed is:

1. A plant cell comprising either:
   (a) two expression units, wherein
      (i) a first expression unit comprises a first promoter operably linked to a first polynucleotide which encodes putrescine aminotransferase comprising the amino acid sequence set forth in SEQ ID NO:51; and
      ii) a second expression unit comprises a second promoter operably linked to a second polynucleotide which encodes gamma-aminobutyricaldehyde dehydrogenase comprising the amino acid sequence set forth in SEQ ID NO:52; or
   (b) a single expression unit which comprises a third promoter operably linked to a third polynucleotide which encodes putrescine aminotransferase comprising the amino acid sequence set forth in SEQ ID NO:51.

2. The plant cell of claim 1, wherein the putrescine aminotransferase is encoded by a polynucleotide comprising the nucleotide sequence set forth in SEQ ID NO:45.

3. The plant cell of claim 1, wherein the gamma-aminobutyricaldehyde dehydrogenase is encoded by a polynucleotide comprising the nucleotide sequence set forth in SEQ ID NO:50.

4. The plant cell of claim 1, wherein the putrescine aminotransferase is encoded by a polynucleotide comprising the nucleotide sequence set forth in SEQ ID NO:45 and the gamma-aminobutyricaldehyde dehydrogenase is encoded by a polynucleotide comprising the nucleotide sequence set forth in SEQ ID NO:50.

5. The plant cell of claim 1, wherein the cell comprises the single expression unit.

6. The plant cell of claim 1, wherein at least one of the first, second, and third promoters is a constitutive promoter.

7. The plant cell of claim 1, wherein at least one of the first, second, and third promoters is a non-constitutive promoter.

8. The plant cell of claim 7, wherein the non-constitutive promoter is selected from the group consisting of a tissue-preferred promoter, a tissue-specific promoter, a cell type-specific promoter, an inducible promoter, or a plant GAD promoter.

9. The plant cell of claim 1, which comprises the two expression units, wherein the first polynucleotide further encodes a first peptide sequence and the second polynucleotide further encodes a second peptide sequence, wherein the first and second peptide sequences transport the putrescine aminotransferase and the gamma-aminobutyricaldehyde dehydrogenase to a specific location in the cell, wherein the specific location is selected from the group consisting of an apoplast, a vacuole, a plastid, a chloroplast, a proplastid, an etioplast, a chromoplast, a mitochondrion, a peroxisome, a glyoxysome, a nucleus, a lysosome, an endomembrane system, an endoplasmic reticulum, a vesicle, and a Golgi apparatus.

10. The plant cell of claim 1, which comprises the single expression unit, wherein the third polynucleotide further encodes a first peptide sequence which will transport the putrescine aminotransferase to a specific location in the cell, wherein the specific location is selected from the group consisting of an apoplast, a vacuole, a plastid, a chloroplast, a proplastid, an etioplast, a chromoplast, a mitochondrion, a peroxisome, a glyoxysome, a nucleus, a lysosome, an endomembrane system, an endoplasmic reticulum, a vesicle, and a Golgi apparatus.

11. The plant cell of claim 1 which is in vitro.

12. The plant cell of claim 1 which is in vivo.

13. The plant cell of claim 1, wherein the plant is selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussels sprouts, cabbage, camelina, canola, cantaloupe, carrot, cassaya, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

14. A method for producing GABA, comprising incorporating into a plant cell either:
   (a) two expression units, wherein
      (i) a first expression unit comprises a first promoter operably linked to a first polynucleotide which encodes putrescine aminotransferase comprising the amino acid sequence set forth in SEQ ID NO:51; and
      (ii) a second expression unit comprises a second promoter operably linked to a second polynucleotide which encodes gamma-aminobutyricaldehyde dehydrogenase comprising the amino acid sequence set forth in SEQ ID NO:52; or
   (b) a single expression unit which comprises a third promoter operably linked to a third polynucleotide which encodes putrescine aminotransferase aminotransferase comprising the amino acid sequence set forth in SEQ ID NO:51,
   whereby the plant cell produces GABA.

15. The method of claim 14, wherein the plant is selected from the group consisting of acacia, alfalfa, aneth, apple, apricot, artichoke, arugula, asparagus, avocado, banana, barley, beans, beech, beet, Bermuda grass, blackberry, blueberry, Blue grass, broccoli, brussels sprouts, cabbage, camelina, canola, cantaloupe, carrot, cassaya, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

16. The method of claim 14, wherein the putrescine aminotransferase is encoded by a polynucleotide comprising the nucleotide sequence set forth in SEQ ID NO:45.

17. The method of claim 14, wherein the gamma-aminobutyricaldehyde dehydrogenase is encoded by a polynucleotide comprising the nucleotide sequence set forth in SEQ ID NO:50.

18. The method of claim 14, wherein the putrescine aminotransferase is encoded by a polynucleotide comprising the nucleotide sequence set forth in SEQ ID NO:45 and the gamma-aminobutyricaldehyde dehydrogenase is encoded by a polynucleotide comprising the nucleotide sequence set forth in SEQ ID NO:50.

19. The method of claim 14, wherein the plant cell comprises the single expression unit.

20. The method of claim 14, wherein at least one of the first, second, and third promoters is a constitutive promoter.

21. The method of claim 14, wherein at least one of the first, second, and third promoters is a non-constitutive promoter.

22. The method of claim 21, wherein the non-constitutive promoter is selected from the group consisting of a tissue-preferred promoter, a tissue-specific promoter, a cell type-specific promoter, an inducible promoter, or a plant GAD promoter.

23. The method of claim 14, wherein the plant cell is in vitro.

24. The method of claim 14, wherein the plant cell is in vivo.

25. A method of treating a plant comprising exogenously applying a polyamine, an amino acid or a combination thereof to a plant comprising the plant cell of claim 1, thereby resulting in altered plant growth and development, increased tolerance to biotic or abiotic stress, and increased yield and biomass.

26. The method of claim 25, wherein the amino acid is selected from the group consisting of glutamate, glutamine, serine, and glycine.

27. A transgenic plant comprising the plant cell of claim 1.

28. The transgenic plant of claim 27, wherein the plant has increased yield.

29. The transgenic plant of claim 27, wherein the plant has increased biomass.

30. The transgenic plant of claim 27, wherein the plant has increased root weight or length.

31. The transgenic plant of claim 27, wherein the plant has increased drought tolerance.

32. The transgenic plant of claim 27, wherein the plant has increased tolerance to elevated temperature.

33. The transgenic plant of claim 27, wherein the plant has increased tolerance to biotic stresses, insect feeding or nematode infestation.

34. The transgenic plant of claim 27, wherein the plant has increased tolerance to limited nutrient availability.

35. The plant cell of claim 1, wherein the plant cell comprises the two expression units.

36. The method of claim 14, wherein the plant cell comprises the two expression units.

37. A method of treating a plant comprising exogenously applying GABA to a plant comprising the plant cell of claim 1, thereby resulting in altered plant growth and development, increased tolerance to biotic or abiotic stress, and increased yield and biomass.

38. The method of claim 14, which comprises the two expression units, wherein the first polynucleotide further encodes a first peptide sequence and the second polynucleotide further encodes a second peptide sequence, wherein the first and second peptide sequences transport the putrescine aminotransferase and the gamma-aminobutyricaldehyde dehydrogenase to a specific location in the cell, wherein the specific location is selected from the group consisting of an apoplast, a vacuole, a plastid, a chloroplast, a proplastid, an etioplast, a chromoplast, a mitochondrion, a peroxisome, a glyoxysome, a nucleus, a lysosome, an endomembrane system, an endoplasmic reticulum, a vesicle, and a Golgi apparatus.

39. The method of claim 14, which comprises the single expression unit, wherein the third polynucleotide further encodes a first peptide sequence which will transport the putrescine aminotransferase to a specific location in the cell, wherein the specific location is selected from the group consisting of an apoplast, a vacuole, a plastid, a chloroplast, a proplastid, an etioplast, a chromoplast, a mitochondrion, a peroxisome, a glyoxysome, a nucleus, a lysosome, an endomembrane system, an endoplasmic reticulum, a vesicle, and a Golgi apparatus.

* * * * *